United States Patent
Liu et al.

(10) Patent No.: US 9,637,486 B2
(45) Date of Patent: May 2, 2017

(54) BTK INHIBITORS

(71) Applicant: MERCK SHARP & DOHME CORP., Rahway, NJ (US)

(72) Inventors: Jian Liu, Edison, NJ (US); Ronald M. Kim, Summit, NJ (US); Joseph Kozlowski, Princeton, NJ (US); Arto D. Krikorian, Astoria, NY (US); Rajan Anand, Fanwood, NJ (US)

(73) Assignee: MERCK SHARP & DOHME CORP., Rahway, NJ (US)

( * ) Notice: Subject to any disclaimer, the term of this patent is extended or adjusted under 35 U.S.C. 154(b) by 0 days.

(21) Appl. No.: 15/105,370

(22) PCT Filed: Dec. 16, 2014

(86) PCT No.: PCT/US2014/070447
§ 371 (c)(1),
(2) Date: Jun. 16, 2016

(87) PCT Pub. No.: WO2015/095099
PCT Pub. Date: Jun. 25, 2015

(65) Prior Publication Data
US 2016/0311820 A1    Oct. 27, 2016

Related U.S. Application Data

(60) Provisional application No. 61/919,346, filed on Dec. 20, 2013.

(51) Int. Cl.
| C07D 471/04 | (2006.01) |
| C07D 519/00 | (2006.01) |
| A61K 31/4375 | (2006.01) |
| A61K 31/4545 | (2006.01) |
| A61K 45/06 | (2006.01) |

(52) U.S. Cl.
CPC ........ *C07D 471/04* (2013.01); *A61K 31/4375* (2013.01); *A61K 31/4545* (2013.01); *A61K 45/06* (2013.01); *C07D 519/00* (2013.01)

(58) Field of Classification Search
None
See application file for complete search history.

(56) References Cited

U.S. PATENT DOCUMENTS

| 2008/0076921 A1 | 3/2008 | Honigberg et al. |
| 2014/0206681 A1 | 7/2014 | Kim et al. |

FOREIGN PATENT DOCUMENTS

| CN | 101674834 | 6/2013 |
| WO | WO2005014599 | 2/2005 |
| WO | WO2007064883 A2 | 6/2007 |
| WO | WO2007064993 A2 | 6/2007 |
| WO | WO2008121742 | 10/2008 |
| WO | WO2011095556 A1 | 8/2011 |
| WO | WO2011153514 A1 | 12/2011 |
| WO | WO2013010380 A1 | 1/2013 |
| WO | WO2013010868 | 1/2013 |
| WO | WO2013010869 | 1/2013 |
| WO | WO2013010898 | 1/2013 |
| WO | WO2014113932 | 7/2014 |
| WO | WO2014116504 | 7/2014 |
| WO | WO2015095099 | 6/2015 |
| WO | WO2015095102 | 6/2015 |

OTHER PUBLICATIONS

Dorwald, Side reactions in Organic Synthesis: A Guide to Successful Synthesis Design, 2005, Chapter 1.
Hackam, Translation of Research Evidence From Animals to Humans, JAMA, 2006, 1731-1733, 296(14).
Jordan, VC, Tamoxifen: A Most Unlikely Pioneering Medicine, Nature Reviews: Drug Discovery, 2003, 205-213, 2.

*Primary Examiner* — Kristin Vajda
(74) *Attorney, Agent, or Firm* — Matthew A. Leff; John C. Todaro

(57) ABSTRACT

The present invention provides Bruton's Tyrosine Kinase (Btk) inhibitor compounds according to Formula I or pharmaceutically acceptable salts thereof. Formula I or a pharmaceutically acceptable salt thereof or to pharmaceutical compositions comprising these compounds and to their use in therapy. In particular, the present invention relates to the use of Btk inhibitor compounds in the treatment of Btk mediated disorders.

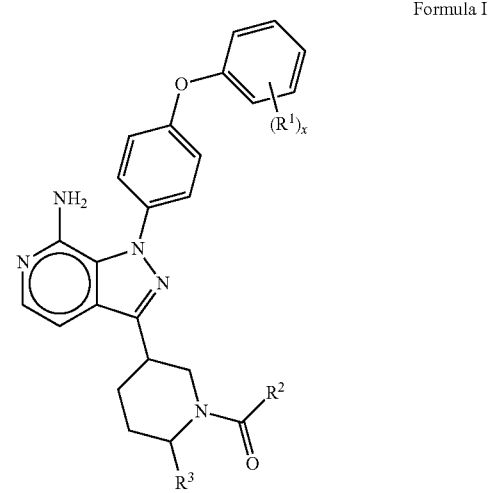

Formula I

10 Claims, No Drawings

SEQUENCE LISTING

<160> NUMBER OF SEQ ID NOS: 1

<210> SEQ ID NO 1
<211> LENGTH: 15
<212> TYPE: PRT
<213> ORGANISM: ARTIFICIAL SEQUENCE
<220> FEATURE:
<223> OTHER INFORMATION: BIOTINYLATED A5 PEPTIDE

<400> SEQUENCE: 1

Glu Gln Glu Asp Glu Pro Glu Gly Asp Tyr Phe Glu Trp Leu Glu
1               5                   10                  15

BTK INHIBITORS

FIELD OF THE INVENTION

The present invention relates to Btk inhibitor compounds, to pharmaceutical compositions comprising these compounds and to their use in therapy. In particular, the present invention relates to the use of Btk inhibitor compounds in the treatment of Bruton's Tyrosine Kinase (Btk) mediated disorders.

BACKGROUND OF THE INVENTION

B lymphocyte activation is key in the generation of adaptive immune responses. Derailed B lymphocyte activation is a hallmark of many autoimmune diseases and modulation of this immune response is therefore of therapeutic interest. Recently the success of B cell therapies in autoimmune diseases has been established. Treatment of rheumatoid arthritis (RA) patients with Rituximab (anti-CD20 therapy) is an accepted clinical therapy by now. More recent clinical trial studies show that treatment with Rituximab also ameliorates disease symptoms in relapsing remitting multiple sclerosis (RRMS) and systemic lupus erythematosus (SLE) patients. This success supports the potential for future therapies in autoimmune diseases targeting B cell immunity.

Bruton tyrosine kinase (Btk) is a Tec family non-receptor protein kinase, expressed in B cells and myeloid cells. The function of Btk in signaling pathways activated by the engagement of the B cell receptor (BCR) and FcεR1 on mast cells is well established. In addition, a function for Btk as a downstream target in Toll like receptor signaling was suggested. Functional mutations in Btk in human results in the primary immunodeficiency disease called XLA which is characterized by a defect in B cell development with a block between pro- and pre-B cell stage. This results in an almost complete absence of B lymphocytes in human causing a pronounced reduction of serum immunoglobulin of all classes. These finding support the key role for Btk in the regulation of the production of auto-antibodies in autoimmune diseases. In addition, regulation of Btk may affect BCR-induced production of pro-inflammatory cytokines and chemokines by B cells, indicating a broad potential for Btk in the treatment of autoimmune diseases.

With the regulatory role reported for Btk in FcεR-mediated mast cell activation, Btk inhibitors may also show potential in the treatment of allergic responses [Gilfillan et al, Immunological Reviews 288 (2009) pp 149-169].
Furthermore, Btk is also reported to be implicated in RANKL-induced osteoclast differentiation [Shinohara et al, Cell 132 (2008) pp 794-806] and therefore may also be of interest for the treatment of bone resorption disorders.

Other diseases with an important role for dysfunctional B cells are B cell malignancies. Indeed anti-CD20 therapy is used effectively in the clinic for the treatment of follicular lymphoma, diffuse large B-cell lymphoma and chronic lymphocytic leukemia [Lim et al, Haematologica, 95 (2010) pp 135-143]. The reported role for Btk in the regulation of proliferation and apoptosis of B cells indicates there is potential for Btk inhibitors in the treatment of B cell lymphomas as well Inhibition of Btk seems to be relevant in particular for B cell lymphomas due to chronic active BCR signaling [Davis et al, Nature, 463 (2010) pp 88-94].

Some classes of Btk inhibitor compounds have been described as kinase inhibitors e.g. Imidazo[1,5-f][1,2,4] triazine compounds have been described in WO2005097800 and WO2007064993. Imidazo[1,5-a]pyrazine compounds have been described in WO2005037836 and WO2001019828 as IGF-1R enzyme inhibitors.

Some of the Btk inhibitors reported are not selective over Src-family kinases. With dramatic adverse effects reported for knockouts of Src-family kinases, especially for double and triple knockouts, this is seen as prohibitive for the development of Btk inhibitors that are not selective over the Src-family kinases.

Both Lyn-deficient and Fyn-deficient mice exhibit autoimmunity mimicking the phenotype of human lupus nephritis. In addition, Fyn-deficient mice also show pronounced neurological defects. Lyn knockout mice also show an allergic-like phenotype, indicating Lyn as a broad negative regulator of the IgE-mediated allergic response by controlling mast cell responsiveness and allergy-associated traits [Odom et al, J. Exp. Med., 199 (2004) pp 1491-1502]. Furthermore, aged Lyn knock-out mice develop severe splenomegaly (myeloid expansion) and disseminated monocyte/macrophage tumors [Harder et al, Immunity, 15 (2001) pp 603-615]. These observations are in line with hyperresponsive B cells, mast cells and myeloid cells, and increased Ig levels observed in Lyn-deficient mice. Female Src knockout mice are infertile due to reduced follicle development and ovulation [Roby et al, Endocrine, 26 (2005) pp 169-176]. The double knockouts $Src^{-/-}$ $Fyn^{-/-}$ and $Src^{-/-}$ $Yes^{-/-}$ show a severe phenotype with effects on movement and breathing. The triple knockouts $Src^{-/-}$ $Fyn^{-/-}$ $Yes^{-/-}$ die at day 9.5 [Klinghoffer et al, EMBO J., 18 (1999) pp 2459-2471]. For the double knockout $Src^{-/-}$ $Hck^{-/-}$, two thirds of the mice die at birth, with surviving mice developing osteopetrosis, extramedullary hematopoiseis, anemia, leukopenia [Lowell et al, Blood, 87 (1996) pp 1780-1792].

Hence, an inhibitor that inhibits multiple or all kinases of the Src-family kinases simultaneously may cause serious adverse effects.

SUMMARY OF THE INVENTION

The present invention provides compounds which inhibit Btk activity, their use for treatment of Btk mediated diseases and disorders, in particular autoimmune diseases and inflammatory diseases, as well as pharmaceutical compositions comprising such compounds and pharmaceutical carriers.

DETAILED DESCRIPTION

The object of the present invention is to provide Bruton's Tyrosine Kinase (Btk) inhibitor compounds, to pharmaceutical compositions comprising these compounds and to their use in therapy. In particular, the present invention relates to the use of Btk inhibitor compounds in the treatment of Btk mediated disorders.

More specifically, the present invention provides Btk inhibitor compounds according to Formula I or pharmaceutically acceptable salts thereof

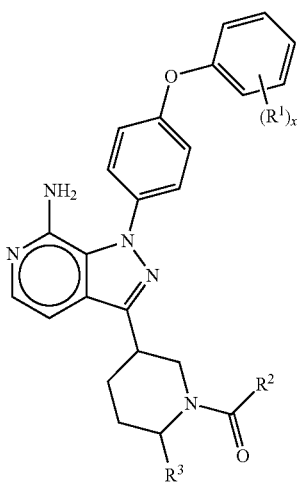

Formula I wherein:
R¹ is halogen;
R² is H is selected from the group consisting of
  a) OH;
  b) (1-6C)alkyl;
  c) (3-6C)cycloalkyl;
  d) (1-6C)alkoxy;
  e) (1-3C)heterocycloalkyl; and
  f) (1-3C)heteroaryl;
  g) (2-4C)alkenyl; and
  h) (2-4C)alkynyl;
R² is optionally substituted with one, two or three groups selected from: halogen, (1-6C)alkyl, (1-6C)alkoxy, hydroxy or cyano;
R³ is H or (1-3C)alkyl;
R² and R³ together can form a saturated heterocyclic 5- or 6-membered ring; and
x is 1, 2 or 3.

The terms used herein have their ordinary meaning and the meaning of such terms is independent at each occurrence thereof. That notwithstanding, and except where stated otherwise, the following definitions apply throughout the specification and claims. Chemical names, common names, and chemical structures may be used interchangeably to describe the same structure. If a chemical compound is referred to using both a chemical structure and a chemical name, and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "hydroxyalkyl," "fluoroalkyl," "alkoxy", etc.

As used herein, and throughout this disclosure, the following terms, unless otherwise indicated, shall be understood to have the following meanings:

Halogen means fluorine, chlorine, bromine or iodine. Fluorine, chlorine or bromine being preferred halogens, fluorine being more preferred.

The term "alkyl," as used herein, refers to an aliphatic hydrocarbon group having one of its hydrogen atoms replaced with a bond having the specified number of carbon atoms. In different embodiments, an alkyl group contains, for example, from 1 to 6 carbon atoms (1-6C)Alkyl or from 1 to 3 carbon atoms (1-3C)Alkyl. Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. In one embodiment, an alkyl group is linear. In another embodiment, an alkyl group is branched.

Unless specified otherwise, "alkyl" includes both branched- and straight-chain saturated aliphatic hydrocarbon groups, including all isomers, having the specified number of carbon atoms; for example, "(1-6C)Alkyl" includes all of the hexyl alkyl and pentyl alkyl isomers as well as n-, iso-, sec- and t-butyl, n- and isopropyl, ethyl and methyl. "Alkylene" refers to both branched- and straight-chain saturated aliphatic hydrocarbon groups, including all isomers, having the specified number of carbons, and having two terminal end chain attachments; for example, the term "A-C₄alkylene-B" represents, for example, A-CH₂—CH₂—CH₂—CH₂—B, A-CH₂—CH₂—CH(CH₃)—CH₂—B, A-CH₂—CH(CH₂CH₃)—B, A-CH₂—C(CH₃)(CH₃)—B, and the like.

"Alkoxy" represents a linear or branched alkyl group of indicated number of carbon atoms attached through an oxygen bridge; for example "(1-6C)Alkoxy" includes —OCH₃, —OCH₂CH₃, —OCH(CH₃)₂, —O(CH₂)₅CH₃, and the like.

Unless otherwise specifically noted as only "unsubstituted" or only "substituted", alkyl groups are unsubstituted or substituted with 1 to 3 substituents on each carbon atom.

The term "alkenyl" means a straight or branched carbon chain having the specified number of carbon atoms with at least one carbon-carbon double bond. Examples of alkenyl include, but are not limited to, vinyl, allyl, isopropenyl, pentenyl, hexenyl, heptenyl, 1-propenyl, 2-butenyl, 2-methyl-2-butenyl, 2,4-hexadienyl, and the like.

The term "alkynyl" means a straight or branched carbon chain having the specified number of carbon atoms with at least one carbon-carbon triple bond. Examples of alkynyl include, but are not limited to ethynyl, propargyl, 1-propynyl, 2-butynyl, and the like.

The term "cycloalkyl" means a cyclic ring of an alkane having the specified total ring carbon atoms; for example; for example, "(3-6C)Cycloalkyl" includes cyclopropyl, cyclobutyl, cyclopentyl, or cyclohexyl.

The term "heterocycloalkyl" means a heterocycloalkyl group having the specified number of carbon atoms; for example, (1-3C)heterocycloalkyl" includes heterocycloalkyl with 1-3 carbon atoms and 1-3 heteroatoms selected from N, O and/or S, which may be attached via a nitrogen if feasible, or a carbon atom. Preferred number of heteroatoms is one or two. Preferred heteroatoms are N or O.

The term (1-3C)heteroaryl means an aromatic group having 1-3 carbon atoms and 1-3 heteroatoms selected from N, O and S, like imidazolyl, thiadiazolyl, pyridinyl, pyrimidinyl, thiophenyl or furyl, pyrazolyl, isoxazolyl or quinolyl. Preferred number of heteroatoms is one or two. Preferred heteroaryl groups are imidazolyl and isoxazolyl. The (1-3C) heteroaryl group may be attached via a carbon atom or a nitrogen, if feasible.

In the above definitions with multifunctional groups, the attachment point is at the last group, unless otherwise specified on the substituent group by a dash. A dash on the substituent group would then represent the point of attachment.

When, in the definition of a substituent, is indicated that "all of the alkyl groups" of said substituent are optionally substituted, this also includes the alkyl moiety of an alkoxy group.

A circle in a ring of Formula I indicates that the ring is aromatic.

The term "substituted" means that one or more hydrogens on the designated atom/atoms is/are replaced with a selection from the indicated group, provided that the designated atom's normal valency under the existing circumstances is not exceeded, and that the substitution results in a stable compound. Combinations of substituents and/or variables are permissible only if such combinations result in stable compounds. "Stable compound" or "stable structure" is defined as a compound or structure that is sufficiently robust to survive isolation to a useful degree of purity from a reaction mixture, and formulation into an efficacious therapeutic agent.

The term "optionally substituted" means optional substitution with the specified groups, radicals or moieties.

The term pharmaceutically acceptable salt is well known in the art. They may be obtained during the final isolation and purification of the compounds of the invention, or separately by reacting the free base function with a suitable mineral acid such as hydrochloric acid, phosphoric acid, or sulfuric acid, or with an organic acid such as for example ascorbic acid, citric acid, tartaric acid, lactic acid, maleic acid, malonic acid, fumaric acid, glycolic acid, succinic acid, propionic acid, acetic acid, methanesulfonic acid, and the like. The acid function can be reacted with an organic or a mineral base, like sodium hydroxide, potassium hydroxide or lithium hydroxide.

The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The term "effective amount" as used herein, refers to an amount of the compound of Formula (I) and/or an additional therapeutic agent, or a composition thereof, that is effective in producing the desired therapeutic, ameliorative, inhibitory or preventative effect when administered to a subject suffering from an RORgammaT-mediated disease or disorder. In the combination therapies of the present invention, as effective amount can refer to each individual agent or to the combination as a whole, wherein the amounts of all agents administered are together effective, but wherein the component agent of the combination may not be present individually in an effective amount.

A "subject" is a human or non-human mammal. In one embodiment, a subject is a human.

It should be noted that any carbon as well as heteroatom with unsatisfied valences in the text, schemes, examples and tables herein is assumed to have the sufficient number of hydrogen atom(s) to satisfy the valences.

The compounds of this invention include the prodrugs, hydrates or solvates of the compounds.

Aspects of the Invention

In one aspect the invention relates to a compound according to Formula I wherein $R^1$ is halogen. In a preferred aspect, the halogen is fluorine.

In another aspect, the invention relates to a compound according to Formula I wherein $R^3$ is $CH_3$.

The invention also relates to those compounds wherein all specific definitions for $R^1$, $R^2$, $R^3$ and x, and all substituent groups in the various aspects of the inventions defined here above occur in any combination within the definition of the Btk inhibitor compounds of Formula I or pharmaceutically acceptable solvates or salts thereof.

Non-limiting examples of the compounds of the present invention include:

3-{(3R)-1-[(3-methyloxetan-3-yl)carbonyl]piperidin-3-yl}-1-(4-phenoxyphenyl)-1H-pyrazolo[3,4-c]pyridin-7-amine;

1-(4-phenoxyphenyl)-3-[(3R)-1-propanoylpiperidin-3-yl]-1H-pyrazolo[3,4-c]pyridin-7-amine;

3-[(3R)-1-(cyclopropylcarbonyl)piperidin-3-yl]-1-(4-phenoxyphenyl)-1H-pyrazolo[3,4-c]pyridin-7-amine;

3-{(3R)-1-[(2,2-difluorocyclopropyl)carbonyl]piperidin-3-yl}-1-(4-phenoxyphenyl)-1H-pyrazolo[3,4-c]pyridin-7-amine;

1-({(3R)-3-[7-amino-1-(4-phenoxyphenyl)-1H-pyrazolo[3,4-c]pyridin-3-yl]piperidin-1-yl}carbonyl)cyclopropanol;

3-{(3R)-1-[(3,5-dimethylisoxazol-4-yl)carbonyl]piperidin-3-yl}-1-(4-phenoxyphenyl)-1H-pyrazolo[3,4-c]pyridin-7-amine;

3-[(3R)-1-(3-methoxypropanoyl)piperidin-3-yl]-1-(4-phenoxyphenyl)-1H-pyrazolo[3,4-c]pyridin-7-amine;

3-{(3R)-1-[(1-methylcyclopropyl)carbonyl]piperidin-3-yl}-1-(4-phenoxyphenyl)-1H-pyrazolo[3,4-c]pyridin-7-amine;

3-{(3R)-1-[(3,3-difluorocyclobutyl)carbonyl]piperidin-3-yl}-1-(4-phenoxyphenyl)-1H-pyrazolo[3,4-c]pyridin-7-amine;

1-({(3R)-3-[7-amino-1-(4-phenoxyphenyl)-1H-pyrazolo[3,4-c]pyridin-3-yl]piperidin-1-yl}carbonyl)cyclopropanecarbonitrile;

3-[(3R)-1-(methoxyacetyl)piperidin-3-yl]-1-(4-phenoxyphenyl)-1H-pyrazolo[3,4-c]pyridin-7-amine;

3-[(3R)-1-(2-methylpropanoyl)piperidin-3-yl]-1-(4-phenoxyphenyl)-1H-pyrazolo[3,4-c]pyridin-7-amine;

3-[(3R)-1-(cyclobutylcarbonyl)piperidin-3-yl]-1-(4-phenoxyphenyl)-1H-pyrazolo[3,4-c]pyridin-7-amine;

3-[(3R)-1-acetylpiperidin-3-yl]-1-(4-phenoxyphenyl)-1H-pyrazolo[3,4-c]pyridin-7-amine;

3-{(3R)-1-[(2-methoxyethoxy)acetyl]piperidin-3-yl}-1-(4-phenoxyphenyl)-1H-pyrazolo[3,4-c]pyridin-7-amine;

3-[(3R)-1-(ethoxyacetyl)piperidin-3-yl]-1-(4-phenoxyphenyl)-1H-pyrazolo[3,4-c]pyridin-7-amine;

(2R)-1-{(3R)-3-[7-amino-1-(4-phenoxyphenyl)-1H-pyrazolo[3,4-c]pyridin-3-yl]piperidin-1-yl}-1-oxopropan-2-ol;

(2S)-1-{(3R)-3-[7-amino-1-(4-phenoxyphenyl)-1H-pyrazolo[3,4-c]pyridin-3-yl]piperidin-1-yl}-1-oxopropan-2-ol;

3-{(3R)-1-[(1-methyl-1H-imidazol-5-yl)carbonyl]piperidin-3-yl}-1-(4-phenoxyphenyl)-1H-pyrazolo[3,4-c]pyridin-7-amine;

3-{(3R)-1-[(1,4-dimethyl-1H-imidazol-5-yl)carbonyl]piperidin-3-yl}-1-(4-phenoxyphenyl)-1H-pyrazolo[3,4-c]pyridin-7-amine;

3-{(3R)-1-[(2S)-2-methoxypropanoyl]piperidin-3-yl}-1-(4-phenoxyphenyl)-1H-pyrazolo[3,4-c]pyridin-7-amine;

3-{(3R)-1-[(2R)-2-methoxypropanoyl]piperidin-3-yl}-1-(4-phenoxyphenyl)-1H-pyrazolo[3,4-c]pyridin-7-amine;

3-[(3R)-1-acryloylpiperidin-3-yl]-1-(4-phenoxyphenyl)-1H-pyrazolo[3,4-c]pyridin-7-amine;

3-[(3R)-1-but-2-ynoylpiperidin-3-yl]-1-(4-phenoxyphenyl)-1H-pyrazolo[3,4-c]pyridin-7-amine;

1-(4-phenoxyphenyl)-3-[(3R)-piperidin-3-yl]-1H-pyrazolo[3,4-c]pyridin-7-amine;

1-[4-(4-fluorophenoxy)phenyl]-3-{(3R)-1-[(3-methyloxetan-3-yl)carbonyl]piperidin-3-yl}-1H-pyrazolo[3,4-c]pyridin-7-amine;

(6R,8aS)-6-{7-amino-1-[4-(3-fluorophenoxy)phenyl]-1H-pyrazolo[3,4-c]pyridin-3-yl}hexahydroindolizin-3(2H)-one;

1-[4-(3-fluorophenoxy)phenyl]-3-{(3R,6S)-6-methyl-1-[(3-methyloxetan-3-yl)carbonyl]piperidin-3-yl}-1H-pyrazolo[3,4-c]pyridin-7-amine; and (2R)-1-[(2S,5R)-5-{7-amino-1-[4-(3-fluorophenoxy)phenyl]-1H-pyrazolo[3,4-c]pyridin-3-yl}-2-methylpiperidin-1-yl]-1-oxopropan-2-ol.

The Btk inhibitor compounds of the invention having Formula I inhibit the Btk kinase activity. All compounds of the invention have an IC50 of 10 μM or lower. In another aspect the invention relates to compounds of Formula I which have an IC50 of less than 100 nM. In yet another aspect the invention relates to compounds of Formula I which have an IC50 of less than 10 nM.

The term IC50 means the concentration of the test compound that is required for 50% inhibition of its maximum effect in vitro.

In another aspect the invention relates to compounds of Formula I or pharmaceutically acceptable salts thereof, which have an IC50 of less than 100 nM. In yet another aspect the invention relates to the compounds of Formula I or pharmaceutically acceptable salts thereof, which have an IC50 of less than 10 nM.

The term IC50 means the concentration of the test compound that is required for 50% inhibition of its maximum effect in vitro.

Inhibition of kinase activity can be measured using the Immobilized Metal Assay for Phosphochemicals (IMAP) assay. IMAP is a homogeneous fluorescence polarization (FP) assay based on affinity capture of phosphorylated peptide substrates. IMAP uses fluorescein-labeled peptide substrates that, upon phosphorylation by a protein kinase, bind to so-called IMAP nanoparticles, which are derivatized with trivalent metal complexes. Binding causes a change in the rate of the molecular motion of the peptide, and results in an increase in the FP value observed for the fluorescein label attached to the substrate peptide (Gaudet et al. A homogeneous fluorescence polarization assay adaptable for a range of protein serine/threonine and tyrosine kinases. *J. Biomol. Screen* (2003) 8, 164-175).

Also BTK enzymatic activity was determined with the LANCE (Lanthanide Chelate Excite) TR-FRET (Time-resolved fluorescence resonance energy transfer) assay. In this assay, the potency ($IC_{50}$) of each compound was determined from an eleven point (1:3 serial dilution; final compound concentration range in assay from 1 μM to 0.017 nM) titration curve using the following outlined procedure. To each well of a black non-binding surface Corning 384-well microplate (Corning Catalog #3820), 5 nL of compound (2000 fold dilution in final assay volume of 10 μL) was dispensed, followed by the addition of 7.5 μL of 1× kinase buffer (50 mM Hepes 7.5, 10 mM $MgCl_2$, 0.01% Brij-35, 1 mM EGTA, 0.05% BSA & 1 mM DTT) containing 10.18 pg/μL (133.3 pM) of BTK enzyme (recombinant protein from baculovirus-transfected Sf9 cells: full-length BTK, 6HIS-tag cleaved). Following a 60 minute compound & enzyme incubation, each reaction was initiated by the addition of 2.5 μL 1× kinase buffer containing 8 μM biotinylated "A5" peptide (Biotin-EQEDEPEGDYFEWLE-NH2), and 100 μM ATP. The final reaction in each well of 10 μL consists of 100 pM hBTK, 2 μM biotin-A5-peptide, and 25 μM ATP. Phosphorylation reactions were allowed to proceed for 120 minutes. Reactions were immediately quenched by the addition of 20 uL of 1× quench buffer (15 mM EDTA, 25 mM Hepes 7.3, and 0.1% Triton X-100) containing detection reagents (0.626 nM of LANCE-Eu-W1024-anti-phosphoTyrosine antibody, PerkinElmer and 86.8 nM of Streptavidin-conjugated Dylight 650, Dyomics/Thermo-Fisher Scientific). After 60 minutes incubation with detection reagents, reaction plates were read on a PerkinElmer EnVision plate reader using standard TR-FRET protocol. Briefly, excitation of donor molecules (Eu-chelate:anti-phospho-antibody) with a laser light source at 337 nm produces energy that can be transferred to Dylight-650 acceptor molecules if this donor:acceptor pair is within close proximity. Fluorescence intensity at both 665 nm (acceptor) and 615 nm (donor) are measured and a TR-FRET ratio calculated for each well (acceptor intensity/donor intensity). $IC_{50}$ values were determined by 4 parameter robust fit of TR-FRET ratio values vs. ($Log_{10}$) compound concentrations.

The Btk activity can also be determined in B cell lines such as Ramos cells or in primary cell assays, e.g. PBMC or whole blood from human, monkey, rat or mouse or isolated splenocytes from monkey, rat or mouse. Inhibition of Btk activity can be investigated measuring anti-IgM-induced MIP1β production (Ramos, PBMC, splenocytes), $H_2O_2$-induced Btk and PLCγ2 phosphorylation (Ramos cells), or anti-IgM-induced B cell proliferation or CD86 expression on primary B cells (PBMC and splenocytes).

Regulation of Btk activity can also be determined on human, monkey, rat or mouse mast cells following activation FcεR induced degranulation, cytokine production and CD63 induced cell surface expression.

Furthermore, regulation of Btk activity can be determined on CD14+ monocytes differentiated following treatment with M-CSF to osteoclasts and activated with RANKL.

Activity of Btk inhibitors can be investigated in mouse splenocytes following administration in vivo. In a typical experiment mice can be euthanized 3 h following compound administration. Spleens can be extracted from the treated mice for splenocyte isolation. Splenocytes can be plated in 96 well culture plates and stimulated with anti-IgM, without further addition of compounds. Anti-IgM-induced B cell stimulation and inhibition thereof by Btk inhibitors can be measured by B cell proliferation, MIP1β production or CD86 expression on CD19+ splenocyte B cells.

Efficacy of Btk inhibitors can also be investigated in the mouse collagen induced arthritis model using a therapeutic protocol with start of treatment following onset of disease, measuring disease score, X-ray analysis of bone destruction, cartilage breakdown and histology of joints Efficacy of Btk inhibitors on the regulation of activated mast cells can be investigated in vivo using the passive cutaneous anaphylaxis model.

The effect of Btk inhibitors on bone resorption in vivo can be investigated using the rat OVX model. In this model ovariectomized animals develop symptoms of osteoporosis that may be regulated using a Btk inhibitor.

The compounds of Formula I can form salts which are also within the scope of this invention. Reference to a compound of Formula (I) herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula (I) contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Such acidic and basic salts used within the scope of the invention are pharmaceutically acceptable (i.e., non-toxic, physiologically acceptable) salts. Salts of the compounds of Formula (I) may be formed, for example, by reacting a compound of Formula (I) with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) Handbook of Pharmaceutical Salts. Properties, Selection and Use. (2002) Zurich: Wiley-VCH; S. Berge et al, Journal of Pharmaceutical Sciences (1977) 66(1) 1-19; P. Gould, International J. of Pharmaceutics (1986) 33 201-217; Anderson et al, The Practice of Medicinal Chemistry (1996), Academic Press, New York; and in The Orange Book (Food & Drug Administration, Washington, D.C. on their website). These disclosures are incorporated herein by reference.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

The compounds of Formula I may have the ability to crystallize in more than one form, a characteristic known as polymorphism, and it is understood that such polymorphic forms ("polymorphs") are within the scope of Formula I. Polymorphism generally can occur as a response to changes in temperature or pressure or both and can also result from variations in the crystallization process. Polymorphs can be distinguished by various physical characteristics known in the art such as x-ray diffraction patterns, solubility and melting point.

The compounds of Formula I may contain asymmetric or chiral centers, and, therefore, exist in different stereoisomeric forms. It is intended that all stereoisomeric forms of the compounds of Formula I as well as mixtures thereof, including racemic mixtures, form part of the present invention. In addition, the present invention embraces all geometric and positional isomers. For example, if a compound of Formula (I) incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g. chiral auxiliary such as a chiral alcohol or Mosher's acid chloride), separating the diastereomers and converting (e.g. hydrolyzing) the individual diastereomers to the corresponding pure enantiomers. Also, some of the compounds of Formula I may be atropisomers (e.g. substituted biaryls) and are considered as part of this invention. Enantiomers can also be separated by use of chiral HPLC column.

It is also possible that the compounds of Formula I may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

A discussion of prodrugs is provided in T. Higuchi and V. Stella, Pro-drugs as Novel Delivery Systems (1987) 14 of the A.C.S. Symposium Series, and in Bioreversible Carriers in Drug Design, (1987) Edward B. Roche, ed., American Pharmaceutical Association and Pergamon Press. The term "prodrug" means a compound (e.g, a drug precursor) that is transformed in vivo to yield a compound of Formula (I) or a pharmaceutically acceptable salt, hydrate or solvate of the compound. The transformation may occur by various mechanisms (e.g. by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

The compounds having Formula I or the pharmaceutically acceptable salts or solvates thereof may form hydrates or solvates. It is known to those of skill in the art that charged compounds form hydrated species when lyophilized with water, or form solvated species when concentrated in a solution with an appropriate organic solvent. The compounds of this invention include the hydrates or solvates of the compounds listed.

One or more compounds of the invention having Formula I or the pharmaceutically acceptable salts or solvates thereof may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

In the compounds of Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

Certain isotopically-labelled compounds of Formula I (e.g. those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labelled compounds of Formula I can generally be prepared by following procedures analogous to those disclosed in the Schemes and/or in the Examples herinbelow, by substituting an appropriate isotopically labeled reagent for a non-isotopically labeled reagent.

The compounds having Formula I and pharmaceutical compositions thereof can be used to treat or prevent a variety of conditions, diseases or disorders mediated by Bruton's Tyrosine kinase (Btk). Such conditions, diseases or disorders include, but are not limited to: (1) arthritis, including rheumatoid arthritis, juvenile arthritis, psoriatic arthritis and osteoarthritis; (2) asthma and other obstructive airways diseases, including chronic asthma, late asthma, airway hyper-responsiveness, bronchitis, bronchial asthma, allergic asthma, intrinsic asthma, extrinsic asthma, dust asthma, adult respiratory distress syndrome, recurrent airway obstruction, and chronic obstruction pulmonary disease including emphysema; (3) autoimmune diseases or disorders, including those designated as single organ or single cell-type autoimmune disorders, for example Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia including idiopathic thrombopenic purpura, sympathetic ophthalmia, myasthenia gravis, Graves' disease, primary biliary cirrhosis, chronic aggressive hepatitis, ulcerative colitis and membranous glomerulopathy, those designated as involving systemic autoimmune disorder, for example systemic lupus erythematosis, immune thrombocytopenic purpura, rheumatoid arthritis, Sjogren's syndrome, Reiter's syndrome, polymyositis-dermatomyositis, systemic sclerosis, polyarteritis nodosa, multiple sclerosis and bullous pemphigoid, and additional autoimmune diseases, which can be B-cell (humoral) based or T-cell based, including Cogan's syndrome, ankylosing spondylitis, Wegener's granulomatosis, autoimmune alopecia, Type I or juvenile onset diabetes, and thyroiditis; (4) cancers or tumors, including alimentary/gastrointestinal tract cancer, colon cancer, liver cancer, skin cancer including mast cell tumor and squamous cell carcinoma, breast and mammary cancer, ovarian cancer, prostate cancer, lymphoma and leukemia (including but not limited to acute myelogenous leukemia, chronic myelogenous leukemia, mantle cell lymphoma, NHL B cell lymphomas (e.g. precursor B-ALL, marginal zone B cell lymphoma, chronic lymphocytic leukemia, diffuse large B cell lymphoma, Burkitt lymphoma, mediastinal large B-cell lymphoma), Hodgkin lymphoma, NK and T cell lymphomas; TEL-Syk and ITK-Syk fusion driven tumors, myelomas including multiple myeloma, myeloproliferative disorders kidney cancer, lung cancer, muscle cancer, bone cancer, bladder cancer, brain cancer, melanoma including oral and metastatic melanoma, Kaposi's sarcoma, proliferative diabetic retinopathy, and angiogenic-associated disorders including solid tumors, and pancreatic cancer; (5) diabetes, including Type I diabetes and complications from diabetes; (6) eye diseases, disorders or conditions including autoimmune diseases of the eye, keratoconjunctivitis, vernal conjunctivitis, uveitis including uveitis associated with Behcet's disease and lens-induced uveitis, keratitis, herpetic keratitis, conical keratitis, corneal epithelial dystrophy, keratoleukoma, ocular premphigus, Mooren's ulcer, scleritis, Grave's ophthalmopathy, Vogt-Koyanagi-Harada syndrome, keratoconjunctivitis sicca (dry eye), phlyctenule, iridocyclitis, sarcoidosis, endocrine ophthalmopathy, sympathetic ophthalmitis, allergic conjunctivitis, and ocular neovascularization; (7) intestinal inflammations, allergies or conditions including Crohn's disease and/or ulcerative colitis, inflammatory bowel disease, coeliac diseases, proctitis, eosinophilic gastroenteritis, and mastocytosis; (8) neurodegenerative diseases including motor neuron disease, Alzheimer's disease, Parkinson's disease, amyotrophic lateral sclerosis, Huntington's disease, cerebral ischemia, or neurodegenerative disease caused by traumatic injury, strike, glutamate neurotoxicity or hypoxia; ischemic/reperfusion injury in stroke, myocardial ischemica, renal ischemia, heart attacks, cardiac hypertrophy, atherosclerosis and arteriosclerosis, organ hypoxia; (9) platelet aggregation and diseases associated with or caused by platelet activation, such as arteriosclerosis, thrombosis, intimal hyperplasia and restenosis following vascular injury; (10) conditions associated with cardiovascular diseases, including restenosis, acute coronary syndrome, myocardial infarction, unstable angina, refractory angina, occlusive coronary thrombus occurring post-thrombolytic therapy or post-coronary angioplasty, a thrombotically mediated cerebrovascular syndrome, embolic stroke, thrombotic stroke, transient ischemic attacks, venous thrombosis, deep venous thrombosis, pulmonary embolus, coagulopathy, disseminated intravascular coagulation, thrombotic thrombocytopenic purpura, thromboangiitis obliterans, thrombotic disease associated with heparin-induced thrombocytopenia, thrombotic complications associated with extracorporeal circulation, thrombotic complications associated with instrumentation such as cardiac or other intravascular catheterization, intra-aortic balloon pump, coronary stent or cardiac valve, conditions requiring the fitting of prosthetic devices, and the like; (11) skin diseases, conditions or disorders including atopic dermatitis, eczema, psoriasis, scleroderma, pruritus and other pruritic conditions; (12) allergic reactions including anaphylaxis, allergic rhinitis, allergic dermatitis, allergic urticaria, angioedema, allergic asthma, or allergic reaction to insect bites, food, drugs, or pollen; (13) transplant rejection, including pancreas islet transplant rejection, bone marrow transplant rejection, graft-versus-host disease, organ and cell transplant rejection such as bone marrow, cartilage, cornea, heart, intervertebral disc, islet, kidney, limb, liver, lung, muscle, myoblast, nerve, pancreas, skin, small intestine, or trachea, and xeno transplantation; (14) low grade scarring including scleroderma, increased fibrosis, keloids, post-surgical scars, pulmonary fibrosis, vascular spasms, migraine, reperfusion injury, and post-myocardial infarction.

The invention thus provides compounds of Formula (I) and salts, solvates and physiologically functional derivatives thereof for use in therapy, and particularly in the treatment of diseases and conditions mediated by inappropriate Btk activity.

The inappropriate Btk activity referred to herein is any Btk activity that deviates from the normal Btk activity expected in a particular mammalian subject. Inappropriate Btk activity may take the form of, for instance, an abnormal increase in activity, or an aberration in the timing and or control of Btk activity. Such inappropriate activity may result then, for example, from overexpression or mutation of the protein kinase leading to inappropriate or uncontrolled activation.

In a further embodiment, the present invention is directed to methods of regulating, modulating, or inhibiting Btk for the prevention and/or treatment of disorders related to unregulated or inappropriate Btk activity.

In a further embodiment, the present invention provides a method of treatment of a subject suffering from a disorder mediated by Btk activity, which comprises administering to said subject an effective amount of a compound of Formula (I) or a pharmaceutically acceptable salt, solvate, or a physiologically functional derivative thereof.

In a further embodiment, the present invention provides for the use of a compound of Formula (I), or a pharmaceutically acceptable salt or solvate thereof, or a physiologically functional derivative thereof, in the preparation of a medicament for the treatment of a disorder mediated by Btk activity.

In a further embodiment said disorder mediated by Btk activity is asthma. In a further embodiment said disorder is rheumatoid arthritis. In yet another embodiment, said disorder is cancer. In a further embodiment said disorder is ocular conjunctivitis.

Yet another aspect of the present invention provides a method for treating diseases caused by or associated with Fc receptor signaling cascades, including FcϵRI and/or FcgRI-mediated degranulation as a therapeutic approach towards the treatment or prevention of diseases characterized by, caused by and/or associated with the release or synthesis of chemical mediators of such Fc receptor signaling cascades or degranulation. In addition, Btk is known to play a critical role in immunotyrosine-based activation motif (ITAM) signaling, B cell receptor signaling, T cell receptor signaling and is an essential component of integrin beta (1), beta (2), and beta (3) signaling in neutrophils. Thus, compounds of the present invention can be used to regulate Fc receptor, ITAM, B cell receptor and integrin signaling cascades, as well as the cellular responses elicited through these signaling cascades. Non-limiting examples of cellular responses that may be regulated or inhibited include respiratory burst, cellular adhesion, cellular degranulation, cell spreading, cell migration, phagocytosis, calcium ion flux, platelet aggregation and cell maturation.

A further aspect of the invention resides in the use of a compound of Formula I or a pharmaceutically acceptable salt thereof for the manufacture of a medicament to be used for the treatment of Btk-mediated diseases or Btk-mediated conditions.

A further aspect of the invention resides in the use of a compound of Formula I or a pharmaceutically acceptable salt thereof for the manufacture of a medicament to be used for the treatment of chronic B cell disorders in which T cells play a prominent role.

In yet another aspect the invention resides in the use of a compound of Formula I or a pharmaceutically acceptable salt thereof for the manufacture of a medicament to be used for the treatment of Btk-mediated diseases or conditions. These include, but are not limited to, the treatment of B cell lymphomas resulting from chronic active B cell receptor signaling.

Thus, the compounds according to the invention may be used in therapies to treat or prevent diseases Bruton's Tyrosine Kinase (Btk) mediated disorders. Btk mediated disorders or Btk mediated condition as used herein, mean any disease state or other deleterious condition in which B cells, mast cells, myeloid cells or osteoclasts play a central role. These diseases include but are not limited to, immune, autoimmune and inflammatory diseases, allergies, infectious diseases, bone resorption disorders and proliferative diseases.

Immune, autoimmune and inflammatory diseases that may be treated or prevented with the compounds of the present invention include rheumatic diseases (e.g. rheumatoid arthritis, psoriatic arthritis, infectious arthritis, progressive chronic arthritis, deforming arthritis, osteoarthritis, traumatic arthritis, gouty arthritis, Reiter's syndrome, polychondritis, acute synovitis and spondylitis), glomerulonephritis (with or without nephrotic syndrome), Goodpasture's syndrome, (and associated glomerulonephritis and pulmonary hemorrhage), atherosclerosis, autoimmune hematologic disorders (e.g. hemolytic anemia, aplastic anemia, idiopathic thrombocytopenia, chronic idiopathic thrombocytopenic purpura (ITP), and neutropenia), autoimmune gastritis, and autoimmune inflammatory bowel diseases (e.g. ulcerative colitis and Crohn's disease), irritable bowel syndrome, host versus graft disease, allograft rejection, chronic thyroiditis, Graves' disease, Sjorgren's disease, scleroderma, diabetes (type I and type II), active hepatitis (acute and chronic), pancreatitis, primary billiary cirrhosis, myasthenia gravis, multiple sclerosis, systemic lupus erythematosis, psoriasis, atopic dermatitis, dermatomyositis, contact dermatitis, eczema, skin sunburns, vasculitis (e.g. Behcet's disease), ANCA-associated and other vasculitudes, chronic renal insufficiency, Stevens-Johnson syndrome, inflammatory pain, idiopathic sprue, cachexia, sarcoidosis, Guillain-Barré syndrome, uveitis, conjunctivitis, kerato conjunctivitis, otitis media, periodontal disease, Addison's disease, Parkinson's disease, Alzheimer's disease, diabetes, septic shock, myasthenia gravis, pulmonary interstitial fibrosis, asthma, bronchitis, rhinitis, sinusitis, pneumoconiosis, pulmonary insufficiency syndrome, pulmonary emphysema, pulmonary fibrosis, silicosis, chronic inflammatory pulmonary disease (e.g. chronic obstructive pulmonary disease) and other inflammatory or obstructive disease on airways.

Allergies that may be treated or prevented include, among others, allergies to foods, food additives, insect poisons, dust mites, pollen, animal materials and contact allergans, type I hypersensitivity allergic asthma, allergic rhinitis, allergic conjunctivitis.

Infectious diseases that may be treated or prevented include, among others, sepsis, septic shock, endotoxic shock, sepsis by Gram-negative bacteria, shigellosis, meningitis, cerebral malaria, pneumonia, tuberculosis, viral myocarditis, viral hepatitis (hepatitis A, hepatitis B and hepatitis C), HIV infection, retinitis caused by cytomegalovirus, influenza, herpes, treatment of infections associated with severe burns, myalgias caused by infections, cachexia secondary to infections, and veterinary viral infections such as lentivirus, caprine arthritic virus, visna-maedi virus, feline immunodeficiency virus, bovine immunodeficiency virus or canine immunodeficiency virus.

Bone resorption disorders that may be treated or prevented include, among others, osteoporosis, osteoarthritis, traumatic arthritis, gouty arthritis and bone disorders related with multiple myeloma.

Proliferative diseases that may be treated or prevented include, among others, non-Hodgkin lymphoma (in particular the subtypes diffuse large B-cell lymphoma (DLBCL) and mantle cell lymphoma (MCL)), B cell chronic lymphocytic leukemia and acute lymphoblastic leukemia (ALL) with mature B cell, ALL in particular.

In particular the compounds of Formula I or pharmaceutically acceptable salts may be used for the treatment of B cell lymphomas resulting from chronic active B cell receptor signaling.

Included herein are methods of treatment and/or pharmaceutical compositions in which at least one compound of Formula I or a pharmaceutically acceptable salt thereof is administered in combination with at least one other active agent. The other active agent is an anti-inflammatory agent, an immunosuppressant agent, or a chemotherapeutic agent. Anti-inflammatory agents include but are not limited to NSAIDs, non-specific and COX-2 specific cyclooxgenase enzyme inhibitors, gold compounds, corticosteroids, methotrexate, tumor necrosis factor receptor (TNF) receptors antagonists, immunosuppressants and methotrexate.

Examples of NSAIDs include, but are not limited to, ibuprofen, flurbiprofen, naproxen and naproxen sodium, diclofenac, combinations of diclofenac sodium and misoprostol, sulindac, oxaprozin, diflunisal, piroxicam, indomethacin, etodolac, fenoprofen calcium, ketoprofen, sodium nabumetone, sulfasalazine, tolmetin sodium, and hydroxychloroquine. Examples of NSAIDs also include COX-2 specific inhibitors such as celecoxib, valdecoxib, lumiracoxib and/or etoricoxib.

In some embodiments, the anti-inflammatory agent is a salicylate. Salicylates include by are not limited to acetylsalicylic acid or aspirin, sodium salicylate, and choline and magnesium salicylates.

The anti-inflammatory agent may also be a corticosteroid. For example, the corticosteroid may be cortisone, dexamethasone, methylprednisolone, prednisolone, prednisolone sodium phosphate, or prednisone.

In additional embodiments the anti-inflammatory agent is a gold compound such as gold sodium thiomalate or auranofin.

The invention also includes embodiments in which the anti-inflammatory agent is a metabolic inhibitor such as a dihydrofolate reductase inhibitor, such as methotrexate or a dihydroorotate dehydrogenase inhibitor, such as leflunomide.

Other embodiments of the invention pertain to combinations in which at least one anti-inflammatory agent is an anti-C5 monoclonal antibody (such as eculizumab or pexelizumab), a TNF antagonist, such as entanercept, or infliximab, which is an anti-TNF alpha monoclonal antibody.

Still other embodiments of the invention pertain to combinations in which at least one active agent is an immunosuppressant agent, such as an immunosuppressant compound chosen from methotrexate, leflunomide, cyclosporine, tacrolimus, azathioprine, and mycophenolate mofetil.

B-cells and B-cell precursors expressing BTK have been implicated in the pathology of B-cell malignancies, including, but not limited to, B-cell lymphoma, lymphoma (including Hodgkin's and non-Hodgkin's lymphoma), hairy cell lymphoma, multiple myeloma, chronic and acute myelogenous leukemia and chronic and acute lymphocytic leukemia.

BTK has been shown to be an inhibitor of the Fas/APO-1 (CD-95) death inducing signaling complex (DISC) in B-lineage lymphoid cells. The fate of leukemia/lymphoma cells may reside in the balance between the opposing proapoptotic effects of caspases activated by DISC and an upstream anti-apoptotic regulatory mechanism involving BTK and/or its substrates (Vassilev et al., J. Biol. Chem. 1998, 274, 1646-1656).

It has also been discovered that BTK inhibitors are useful as chemosensitizing agents, and, thus, are useful in combination with other chemotherapeutic agents, in particular, drugs that induce apoptosis. Examples of other chemotherapeutic agents that can be used in combination with chemosensitizing BTK inhibitors include topoisomerase I inhibitors (camptothecin or topotecan), topoisomerase II inhibitors (e.g. daunomycin and etoposide), alkylating agents (e.g. cyclophosphamide, melphalan and BCNU), tubulin directed agents (e.g. taxol and vinblastine), and biological agents (e.g. antibodies such as anti CD20 antibody, IDEC 8, immunotoxins, and cytokines).

Btk activity has also been associated with some leukemias expressing the bcr-abl fusion gene resulting from translocation of parts of chromosome 9 and 22. This abnormality is commonly observed in chronic myelogenous leukemia. Btk is constitutively phosphorylated by the bcr-abl kinase which initiates downstream survival signals which circumvents apoptosis in bcr-abl cells. (N. Feldhahn et al. J. Exp. Med. 2005 201(11):1837-1852).

While it is possible that, for use in therapy, a compound of Formula (I), as well as salts, solvates and physiological functional derivatives thereof, may be administered as the raw chemical, it is possible to present the active ingredient as a pharmaceutical composition. Accordingly, the invention further provides a pharmaceutical composition, which comprises a compound of Formula (I) and salts, solvates and physiological functional derivatives thereof, and one or more pharmaceutically acceptable carriers, diluents, or excipients. The compounds of the Formula (I) and salts, solvates and physiological functional derivatives thereof, are as described above. The carrier(s), diluent(s) or excipient(s) must be acceptable in the sense of being compatible with the other ingredients of the formulation and not deleterious to the recipient thereof. In accordance with another aspect of the invention there is also provided a process for the preparation of a pharmaceutical composition including admixing a compound of the Formula (I), or salts, solvates and physiological functional derivatives thereof, with one or more pharmaceutically acceptable carriers, diluents or excipients.

Pharmaceutical compositions of the present invention may be presented in unit dose forms containing a predetermined amount of active ingredient per unit dose. Such a unit may contain, for example, 5 µg to 1 g, preferably 1 mg to 700 mg, more preferably 5 mg to 100 mg of a compound of the Formula (I), depending on the condition being treated, the route of administration and the age, weight and condition of the patient. Such unit doses may therefore be administered more than once a day. Preferred unit dosage compositions are those containing a daily dose or sub-dose (for administration more than once a day), as herein above recited, or an appropriate fraction thereof, of an active ingredient. Furthermore, such pharmaceutical compositions may be prepared by any of the methods well known in the pharmacy art.

Pharmaceutical compositions of the present invention may be adapted for administration by any appropriate route, for example by the oral (including buccal or sublingual), rectal, topical, inhaled, nasal, ocular, sublingual, subcutaneous, local or parenteral (including intravenous and intramuscular) route, and the like, all in unit dosage forms for administration. Such compositions may be prepared by any method known in the art of pharmacy, for example by bringing into association the active ingredient with the carrier(s) or excipient(s). Dosage forms include tablets, troches, dispersions, suspensions, solutions, capsules, creams, ointments, aerosols, and the like.

In a further embodiment, the present invention provides a pharmaceutical composition adapted for administration by the oral route, for treating, for example, rheumatoid arthritis.

In a further embodiment, the present invention provides a pharmaceutical composition adapted for administration by the nasal route, for treating, for example, allergic rhinitis.

In a further embodiment, the present invention provides a pharmaceutical composition adapted for administration by the inhaled route, for treating, for example, asthma, Chronic Obstructive Pulmonary disease (COPD) or Acute Respiratory Distress Syndrome (ARDS).

In a further embodiment, the present invention provides a pharmaceutical composition adapted for administration by the ocular route, for treating, diseases of the eye, for example, conjunctivitis.

In a further embodiment, the present invention provides a pharmaceutical composition adapted for administration by the parenteral (including intravenous) route, for treating, for example, cancer.

For parenteral administration, the pharmaceutical composition of the invention may be presented in unit-dose or multi-dose containers, e.g. injection liquids in predetermined amounts, for example in sealed vials and ampoules, and may also be stored in a freeze dried (lyophilized) condition requiring only the addition of sterile liquid carrier, e.g. water, prior to use.

Mixed with such pharmaceutically acceptable auxiliaries, e.g. as described in the standard reference, Gennaro, A. R. et al., Remington: *The Science and Practice of Pharmacy* (20th Edition., Lippincott Williams & Wilkins, 2000, see especially Part 5: Pharmaceutical Manufacturing), the active agent may be compressed into solid dosage units, such as pills, tablets, or be processed into capsules or suppositories. By means of pharmaceutically acceptable liquids the active agent can be applied as a fluid composition, e.g. as an injection preparation, in the form of a solution, suspension, emulsion, or as a spray, e.g. a nasal spray.

For making solid dosage units, the use of conventional additives such as fillers, colorants, polymeric binders and the like is contemplated. In general any pharmaceutically acceptable additive which does not interfere with the function of the active compounds can be used. Suitable carriers with which the active agent of the invention can be administered as solid compositions include lactose, starch, cellulose derivatives and the like, or mixtures thereof, used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

Pharmaceutical compositions of the present invention which are adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit compositions for oral administration can be microencapsulated. The formulation can also be prepared to prolong or sustain the release, for example, by coating or embedding particulate material in polymers, wax or the like.

The compounds of Formula (I), and salts, solvates and physiological functional derivatives thereof, can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of Formula (I) and salts, solvates and physiological functional derivatives thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Dosage forms for inhaled administration may conveniently be formulated as aerosols or dry powders.

For compositions suitable and/or adapted for inhaled administration, it is preferred that the compound or salt of Formula (I) is in a particle-size-reduced form, and more preferably the size-reduced form is obtained or obtainable by micronisation. The preferable particle size of the size-reduced (e.g. micronised) compound or salt or solvate defined by a D50 value of about 0.5 to about 10 microns (for example as measured using laser diffraction).

Aerosol formulations, e.g. for inhaled administration, can comprise a solution or fine suspension of the active substance in a pharmaceutically acceptable aqueous or non-aqueous solvent. Aerosol formulations can be presented in single or multidose quantities in sterile form in a sealed container, which can take the form of a cartridge or refill for use with an atomising device or inhaler. Alternatively the sealed container may be a unitary dispensing device such as a single dose nasal inhaler or an aerosol dispenser fitted with a metering valve (metered dose inhaler) which is intended for disposal once the contents of the container have been exhausted.

Where the dosage form comprises an aerosol dispenser, it preferably contains a suitable propellant under pressure such as compressed air, carbon dioxide or an organic propellant such as a hydrofluorocarbon (HFC). Suitable HFC propellants include 1,1,1,2,3,3,3-heptafluoropropane and 1,1,1,2-tetrafluoroethane. The aerosol dosage forms can also take the form of a pump-atomiser. The pressurised aerosol may contain a solution or a suspension of the active compound. This may require the incorporation of additional excipients e.g. co-solvents and/or surfactants to improve the dispersion characteristics and homogeneity of suspension formulations. Solution formulations may also require the addition of co-solvents such as ethanol. Other excipient modifiers may also be incorporated to improve, for example, the stability and/or taste and/or fine particle mass characteristics (amount and/or profile) of the formulation.

For pharmaceutical compositions suitable and/or adapted for inhaled administration, it is preferred that the pharmaceutical composition is a dry powder inhalable composition. Such a composition can comprise a powder base such as lactose, glucose, trehalose, mannitol or starch, the compound of Formula (I) or salt or solvate thereof (preferably in particle-size-reduced form, e.g. in micronised form), and optionally a performance modifier such as L-leucine or another amino acid, and/or metals salts of stearic acid such as magnesium or calcium stearate. Preferably, the dry powder inhalable composition comprises a dry powder blend of lactose and the compound of Formula (I) or salt thereof. The lactose is preferably lactose hydrate e.g. lactose monohydrate and/or is preferably inhalation-grade and/or fine-grade lactose. Preferably, the particle size of the lactose is defined by 90% or more (by weight or by volume) of the lactose particles being less than 1000 microns (micrometers) (e.g. 10-1000 microns e.g. 30-1000 microns) in diameter, and/or 50% or more of the lactose particles being less than 500 microns (e.g. 10-500 microns) in diameter. More n) preferably, the particle size of the lactose is defined by 90% or more of the lactose particles being less than 300 microns (e.g. 10-300 microns e.g. 50-300 microns) in diameter, and/or 50% or more of the lactose particles being less than 100 microns in diameter. Optionally, the particle size of the lactose is defined by 90% or more of the lactose particles being less than 100-200 microns in diameter, and/or 50% or more of the lactose particles being less than 40-70 microns in diameter. It is preferable that about 3 to about 30% (e.g. about 10%) (by weight or by volume) of the particles are less than 50 microns or less than 20 microns in diameter. For example, without limitation, a suitable inhalation-grade lactose is E9334 lactose (10% fines) (Borculo Domo Ingredients, Hanzeplein 25, 8017 J D Zwolle, Netherlands).

Optionally, in particular for dry powder inhalable compositions, a pharmaceutical composition for inhaled administration can be incorporated into a plurality of sealed dose containers (e.g. containing the dry powder composition) mounted longitudinally in a strip or ribbon inside a suitable inhalation device. The container is rupturable or peel-openable on demand and the dose of e.g. the dry powder composition can be administered by inhalation via the device such as the DISKUS® device (GlaxoSmithKline). Other dry powder inhalers are well known to those of ordinary skill in the art, and many such devices are commercially available, with representative devices including Aerolizer® (Novartis), Airmax™ (IVAX), ClickHaler® (Innovata Biomed), Diskhaler® (GlaxoSmithKline), Accuhaler (GlaxoSmithKline), Easyhaler® (Orion Pharma), Eclipse™ (Aventis), FlowCaps® (Hovione), Handihaler® (Boehringer Ingelheim), Pulvinal® (Chiesi), Rotahaler® (GlaxoSmithKline), SkyeHaler™ or Certihaler™ (SkyePharma), Twisthaler (Schering-Plough), Turbuhaler® (AstraZeneca), Ultrahaler® (Aventis), and the like.

Dosage forms for ocular administration may be formulated as solutions or suspensions with excipients suitable for ophthalmic use.

Dosage forms for nasal administration may conveniently be formulated as aerosols, solutions, drops, gels or dry powders.

Pharmaceutical compositions adapted for administration by inhalation include fine particle dusts or mists, which may be generated by means of various types of metered, dose pressurized aerosols, nebulizers or insufflators.

For pharmaceutical compositions suitable and/or adapted for intranasal administration, the compound of Formula (I) or a pharmaceutically acceptable salt or solvate thereof may be formulated as a fluid formulation for delivery from a fluid dispenser. Such fluid dispensers may have, for example, a dispensing nozzle or dispensing orifice through which a metered dose of the fluid formulation is dispensed upon the application of a user-applied force to a pump mechanism of the fluid dispenser. Such fluid dispensers are generally provided with a reservoir of multiple metered doses of the fluid formulation, the doses being dispensable upon sequential pump actuations. The dispensing nozzle or orifice may be configured for insertion into the nostrils of the user for spray dispensing of the fluid formulation into the nasal cavity. A fluid dispenser of the aforementioned type is described and illustrated in WO-A-2005/044354, the entire content of which is hereby incorporated herein by reference. The dispenser has a housing which houses a fluid discharge device having a compression pump mounted on a container for containing a fluid formulation. The housing has at least one finger-operable side lever which is movable inwardly with respect to the housing to cam the container upwardly in the housing to cause the pump to compress and pump a metered dose of the formulation out of a pump stem through a nasal nozzle of the housing. A particularly preferred fluid dispenser is of the general type illustrated in FIGS. 30-40 of WO-A-2005/044354.

The invention further includes a pharmaceutical composition of a compound of Formula I or pharmaceutically acceptable salts thereof, as hereinbefore described, in combination with packaging material suitable for said composition, said packaging material including instructions for the use of the composition for the use as hereinbefore described.

The following are examples of representative pharmaceutical dosage forms for the compounds of this invention:

| Injectable Suspension (I.M.) | mg/ml |
|---|---|
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of 1 ml | |

| Tablet | mg/tablet |
|---|---|
| Compound of Formula I | 25 |
| Microcrystalline Cellulose | 415 |
| Providone | 14.0 |
| Pregelatinized Starch | 43.5 |
| Magnesium Stearate | 2.5 |
| | 500 |

| Capsule | mg/capsule |
|---|---|
| Compound of Formula I | 25 |
| Lactose Powder | 573.5 |
| Magnesium Stearate | 1.5 |
| | 600 |

| Aerosol | Per canister |
|---|---|
| Compound of Formula I | 24 mg |
| Lecithin, NF Liquid Concentrate | 1.2 mg |
| Trichlorofluoromethane, NF | 4.025 gm |
| Dichlorodifluoromethane, NF | 12.15 gm |

It will be appreciated that when the compound of the present invention is administered in combination with other therapeutic agents normally administered by the inhaled, intravenous, oral or intranasal route, that the resultant pharmaceutical composition may be administered by the same routes.

It should be understood that in addition to the ingredients particularly mentioned above, the compositions may include other agents conventional in the art having regard to the type of formulation in question, for example those suitable for oral administration may include flavoring agents.

A therapeutically effective amount of a compound of the present invention will depend upon a number of factors including, for example, the age and weight of the animal, the precise condition requiring treatment and its severity, the particular compound having Formula I, the nature of the formulation, and the route of administration, and will ultimately be at the discretion of the attendant physician or veterinarian. However, an effective amount of a compound of Formula (I) for the treatment of diseases or conditions associated with inappropriate Btk activity, will generally be in the range of 5 μg to 100 mg/kg body weight of recipient (mammal) per day and more usually in the range of 5 μg to 10 mg/kg body weight per day. This amount may be given in a single dose per day or more usually in a number (such as two, three, four, five or six) of sub-doses per day such that the total daily dose is the same. An effective amount of a salt or solvate, thereof, may be determined as a proportion of the effective amount of the compound of Formula (I) per se.

In general parenteral administration requires lower dosages than other methods of administration which are more dependent upon absorption. However, a dosage for humans preferably contains 0.0001-25 mg of a compound of Formula I or pharmaceutically acceptable salts thereof per kg body weight. The desired dose may be presented as one dose or as multiple subdoses administered at appropriate intervals throughout the day, or, in case of female recipients, as doses to be administered at appropriate daily intervals throughout the menstrual cycle. The dosage as well as the regimen of administration may differ between a female and a male recipient.

The present invention also relates to a pharmaceutical composition comprising a compound of Formula I or pharmaceutically acceptable salt thereof in admixture with pharmaceutically acceptable auxiliaries and optionally other therapeutic agents. The auxiliaries must be "acceptable" in the sense of being compatible with the other ingredients of the composition and not deleterious to the recipients thereof.

The invention further includes a pharmaceutical composition comprising at least one compound of Formula I or pharmaceutically acceptable salts thereof in combination with at least one other therapeutically active agent.

Compounds of the present invention, and their salts and solvates, and physiologically functional derivatives thereof, may be employed alone or in combination with other therapeutic agents for the treatment of Btk mediated diseases and conditions associated with inappropriate Btk activity. Combination therapies according to the present invention thus comprise the administration of at least one compound of Formula (I) or a pharmaceutically acceptable salt or solvate thereof, or a physiologically functional derivative thereof, and the use of at least one other pharmaceutically active agent. The compound(s) of Formula (I) and the other pharmaceutically active agent(s) may be administered together or separately and, when administered separately this may occur simultaneously or sequentially in any order. The amounts of the compound(s) of Formula (I) and the other pharmaceutically active agent(s) and the relative timings of administration will be selected in order to achieve the desired combined therapeutic effect.

For the treatment of the inflammatory diseases, rheumatoid arthritis, psoriasis, inflammatory bowel disease, COPD, asthma and allergic rhinitis a compound of Formula I may be combined with one or more other active agents such as: (1) TNF-α inhibitors such as infliximab (Remicade®), etanercept (Enbrel®), adalimumab (Humira®), certolizumab pegol (Cimzia®), and golimumab (Simponi®); (2) non-selective COX-I/COX-2 inhibitors (such as piroxicam, diclofenac, propionic acids such as naproxen, flubiprofen, fenoprofen, ketoprofen and ibuprofen, fenamates such as mefenamic acid, indomethacin, sulindac, etodolac, azapropazone, pyrazolones such as phenylbutazone, salicylates such as aspirin); (3) COX-2 inhibitors (such as meloxicam, celecoxib, rofecoxib, valdecoxib and etoricoxib); (4) other agents for treatment of rheumatoid arthritis including methotrexate, leflunomide, sulfasalazine, azathioprine, cyclosporin, tacrolimus, penicillamine, bucillamine, actarit, mizoribine, lobenzarit, ciclesonide, hydroxychloroquine, d-penicillamine, aurothiomalate, auranofin or parenteral or oral gold, cyclophosphamide, Lymphostat-B, BAFF/APRIL inhibitors and CTLA-4-Ig or mimetics thereof; (5) leukotriene biosynthesis inhibitor, 5-lipoxygenase (5-LO) inhibitor or 5-lipoxygenase activating protein (FLAP) antagonist such as zileuton; (6) LTD4 receptor antagonist such as zafirlukast, montelukast and pranlukast; (7) PDE4 inhibitor such as roflumilast, cilomilast, AWD-12-281 (Elbion), and PD-168787 (Pfizer); (8) antihistaminic H1 receptor antagonists such as cetirizine, levocetirizine, loratadine, desloratadine, fexofenadine, astemizole, azelastine, levocabastine, olopatidine, methapyrilene and chlorpheniramine; (9) α1- and α2-adrenoceptor agonist vasoconstrictor sympathomimetic agent, such as propylhexedrine, phenylephrine, phenylpropanolamine, pseudoephedrine, naphazoline hydrochloride, oxymetazoline hydrochloride, tetrahydrozoline hydrochloride, xylometazoline hydrochloride, and ethylnorepinephrine hydrochloride; (10) anticholinergic agents such as ipratropium bromide, tiotropium bromide, oxitropium bromide, aclindinium bromide, glycopyrrolate, (R,R)-glycopyrrolate, pirenzepine, and telenzepine; (11) β-adrenoceptor agonists such as metaproterenol, isoproterenol, isoprenaline, albuterol, formoterol (particularly the fumarate salt), salmeterol (particularly the xinafoate salt), terbutaline, orciprenaline, bitolterol mesylate, fenoterol, and pirbuterol, or methylxanthanines including theophylline and aminophylline, sodium cromoglycate; (12) insulin-like growth factor type I (IGF-1) mimetic; (13) glucocorticosteroids, especially inhaled glucocorticoid with reduced systemic side effects, such as prednisone, prednisolone, flunisolide, triamcinolone acetonide, beclomethasone dipropionate, budesonide, fluticasone propionate, ciclesonide and mometasone furoate; (14) kinase inhibitors such as inhibitors of the Janus Kinases (JAK 1 and/or JAK2 and/or JAK 3 and/or TYK2), p 38 MAPK and IKK2; (15) B-cell targeting biologics such as rituximab (Rituxan®); (16) selective costimulation modulators such as abatacept (Orencia); (17) interleukin inhibitors, such as IL-1 inhibitor anakinra (Kineret) and IL-6 inhibitor tocilizumab (Actemra).

The present invention also provides for "triple combination" therapy, comprising a compound of Formula (I) or a pharmaceutically acceptable salt thereof together with beta$_2$-adrenoreceptor agonist and an anti-inflammatory corticosteroid. Preferably this combination is for treatment and/or prophylaxis of asthma, COPD or allergic rhinitis. The beta$_2$-adrenoreceptor agonist and/or the anti-inflammatory corticosteroid can be as described above and/or as described in WO 03/030939 A1. Representative examples of such a "triple" combination are a compound of Formula (I) or a pharmaceutically acceptable salt thereof in combination with the components of Advair® (salmeterol xinafoate and fluticasone propionate), Symbicort® (budesonide and formoterol fumarate), or Dulera® (mometasone furoate and formoterol).

For the treatment of cancer a compound of Formula I may be combined with one or more of an anticancer agents. Examples of such agents can be found in *Cancer Principles and Practice of Oncology* by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include, but are not limited to, the following: (1) estrogen receptor modulator such as diethylstibestral, tamoxifen, raloxifene, idoxifene, LY353381, LY117081, toremifene, fluoxymestero, and SH646; (2) other hormonal agents including aromatase inhibitors (e.g., aminoglutethimide, tetrazole anastrozole, letrozole and exemestane), luteinizing hormone release hormone (LHRH) analogues, ketoconazole, goserelin acetate, leuprolide, megestrol acetate and mifepristone; (3) androgen receptor modulator such as finasteride and other 5α-reductase inhibitors, nilutamide, flutamide, bicalutamide, liarozole, and abiraterone acetate; (4) retinoid receptor modulator such as bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide; (5) antiproliferative agent such asantisense RNA and DNA oligonucleotides such as G3139, ODN698, RVASKRAS, GEM231, and INX3001, and anti-metabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N6-[4-deoxy-4-[N2-[2(E),4(E)-tetradecadienoyl]glycy-lamino]-L-glycero-B-L-manno-heptopyranosyl]adenine, aplidine, ecteinascidin, troxacitabine, aminopterin, 5-flurouracil, floxuridine, methotrexate, leucovarin, hydroxyurea, thioguanine (6-TG), mercaptopurine (6-MP), cytarabine, pentostatin, fludarabine phosphate, cladribine (2-CDA), asparaginase, gemcitabine, alanosine, swainsonine, lometrexol, dexrazoxane, methioninase, and 3-aminopyridine-2-carboxaldehyde thiosemicarbazone; (6) prenyl-protein transferase inhibitor including farnesyl-protein transferase (FPTase), geranylgeranyl-protein transferase type I (GGPTase-I), and geranylgeranyl-protein transferase type-II (GGPTase-II, also called Rab GGPTase); (7) HMG-CoA reductase inhibitor such as lovastatin, simvastatin, pravastatin, atorvastatin, fluvastatin and rosuvastatin; (8) angiogenesis inhibitor such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, co erythropoietin (epoietin-α), granulocyte-CSF (filgrastin), granulocyte, macrophage-CSF (sargramostim), pentosan polysulfate, cyclooxygenase inhibitors, steroidal anti-inflammatories, carboxyamidotriazole, combretastatin A-4, squalamine, 6-O-chloroacetyl-carbonyl)-fumagillol, thalidomide, angiostatin, troponin-1, angiotensin II antagonists, heparin, carboxypeptidase U inhibitors, and antibodies to VEGF, endostatin, ukrain, ranpirnase, IM862, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RPI4610, NX31838, sulfated mannopentaose phosphate, and 3-[(2,4-dimethylpyrrol-5-yl)methylene]-2-indolinone (SU5416); (9) PPAR-γ agonists, PPAR-δ agonists, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and (2R)-7-(3-(2-chloro-4-(4-fluorophenoxy)phenoxy)propoxy)-2-ethylchromane-2-carboxylic acid (disclosed in U.S. Ser. No. 60/235, 708 and 60/244,697); (9) inhibitor of inherent multidrug resistance including inhibitors of p-glycoprotein (P-gp), such as LY335979, XR9576, OC144-093, R101922, VX853 and PSC833 (valspodar); (10) inhibitor of cell proliferation and survival signaling such as inhibitors of EGFR (for example gefitinib and erlotinib), inhibitors of ERB-2 (for example trastuzumab), inhibitors of IGF1R such as MK-0646 (dalotuzumab), inhibitors of CD20 (rituximab), inhibitors of cytokine receptors, inhibitors of MET, inhibitors of PI3K family kinase (for example LY294002), serine/threonine kinases (including but not limited to inhibitors of Akt such as described in (WO 03/086404, WO 03/086403, WO 03/086394, WO 03/086279, WO 02/083675, WO 02/083139, WO 02/083140 and WO 02/083138), inhibitors of Raf kinase (for example BAY-43-9006), inhibitors of MEK (for example CI-1040 and PD-098059) and inhibitors of mTOR (for example Wyeth CCI-779 and Ariad AP23573); (11) a bisphosphonate such as etidronate, pamidronate, alendronate, risedronate, zoledronate, ibandronate, incadronate or cimadronate, clodronate, EB-1053, minodronate, neridronate, piridronate and tiludronate; (12) γ-secretase inhibitors, (13) agents that interfere with receptor tyrosine kinases (RTKs) including inhibitors of c-Kit, Eph, PDGF, Flt3 and c-Met; (14) agent that interferes with a cell cycle checkpoint including inhibitors of ATR, ATM, the Chk1 and Chk2 kinases and cdk and cdc kinase inhibitors and are specifically exemplified by 7-hydroxystaurosporin, flavopiridol, CYC202 (Cyclacel) and BMS-387032; (15) BTK inhibitors such as PCI32765, AVL-292 and AVL-101; (16) PARP inhibitors including iniparib, olaparib, AGO14699, ABT888 and MK4827; (16) ERK inhibitors; (17) mTOR inhibitors such as sirolimus, ridaforolimus, temsirolimus, everolimus; (18) cytotoxic/cytostatic agents.

"Cytotoxic/cytostatic agents" refer to compounds which cause cell death or inhibit cell proliferation primarily by interfering directly with the cell's functioning or inhibit or interfere with cell mytosis, including alkylating agents, tumor necrosis factors, intercalators, hypoxia activatable compounds, microtubule inhibitors/microtubule-stabilizing agents, inhibitors of mitotic kinesins, inhibitors of histone deacetylase, inhibitors of kinases involved in mitotic progression, antimetabolites; biological response modifiers; hormonal/anti-hormonal therapeutic agents, haematopoietic growth factors, monoclonal antibody targeted therapeutic agents, topoisomerase inhibitors, proteasome inhibitors and ubiquitin ligase inhibitors.

Examples of cytotoxic agents include, but are not limited to, sertenef, cachectin, chlorambucil, cyclophosphamide, ifosfamide, mechlorethamine, melphalan, uracil mustard, thiotepa, busulfan, carmustine, lomustine, streptozocin, tasonermin, lonidamine, carboplatin, altretamine, dacarbazine, procarbazine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum (II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, doxorubicin, daunorubicin, idarubicin, anthracenedione, bleomycin, mitomycin C, dactinomycin, plicatomycin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755, and 4-demethoxy-3-deamino-3-aziridinyl-4-methylsulphonyl-daunorubicin.

An example of a hypoxia activatable compound is tirapazamine.

Examples of proteasome inhibitors include but are not limited to lactacystin and bortezomib.

Examples of microtubule inhibitors/microtubule-stabilising agents include vincristine, vinblastine, vindesine, vinzolidine, vinorelbine, vindesine sulfate, 3',4'-didehydro-4'-deoxy-8'-norvincaleukoblastine, podophyllotoxins (e.g., etoposide (VP-16) and teniposide (VM-26)), paclitaxel, docetaxol, rhizoxin, dolastatin, mivobulin isethionate, auristatin, cemadotin, RPR109881, BMS184476, vinflunine, cryptophycin, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797.

Some examples of topoisomerase inhibitors are topotecan, hycaptamine, irinotecan, rubitecan, 6-ethoxypropionyl-3',4'-O-exo-benzylidene-chartreusin, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, 2,3-(methylenedioxy)-5-methyl-7-hydroxy-8-methoxybenzo[c]-phenanthridinium, 5-(3-aminopropylamino)-7,10-dihydroxy-2-(2-hydroxyethylaminomethyl)-6H-pyrazolo[4,5,1-de]acridin-6-one, N-[1-[2-(diethylamino)ethylamino]-7-methoxy-9-oxo-9H-thioxanthen-4-ylmethyl]-formamide, N-(2-

(dimethylamino)ethyl)acridine-4-carboxamide, 6-[[2-(dimethylamino)ethyl]amino]-3-hydroxy-7H-indeno[2,1-c]quinolin-7-one, and dimesna.

Examples of inhibitors of mitotic kinesins include, but are not limited to inhibitors of KSP, inhibitors of MKLP1, inhibitors of CENP-E, inhibitors of MCAK, inhibitors of Kif14, inhibitors of Mphosph1 and inhibitors of Rab6-KIFL.

Examples of "histone deacetylase inhibitors" include, but are not limited to, vorinostat, trichostatin A, oxamflatin, PXD101, MG98, valproic acid and scriptaid.

"Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1. An example of an "aurora kinase inhibitor" is VX-680.

"Antiproliferative agents" includes antisense RNA and DNA oligonucleotides such as G3139, ODN698, RVASKRAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N6-[4-deoxy-4-[N2-[2,4-tetradecadienoyl]glycylamino]-L-glycero-B-L-manno-heptopyranosyl]adenine, aplidine, ecteinascidin, troxacitabine, aminopterin, 5-flurouracil, floxuridine, methotrexate, leucovarin, hydroxyurea, thioguanine (6-TG), mercaptopurine (6-MP), cytarabine, pentostatin, fludarabine phosphate, cladribine (2-CDA), asparaginase, gemcitabine, alanosine, swainsonine, lometrexol, dexrazoxane, methioninase, and 3-aminopyridine-2-carboxaldehyde thiosemicarbazone.

Non-limiting examples of suitable agents used in cancer therapy that may be combined with compounds of Formula I include, but are not limited to, abarelix; aldesleukin; alemtuzumab; alitretinoin; allopurinol; altretamine; amifostine; anastrozole; arsenic trioxide; asparaginase; azacitidine; bendamustine; bevacuzimab; bexarotene; bleomycin; bortezomib; busulfan; calusterone; capecitabine; carboplatin; carmustine; cetuximab; chlorambucil; cisplatin; cladribine; clofarabine; cyclophosphamide; cytarabine; dacarbazine; dactinomycin, actinomycin D; dalteparin; darbepoetin alfa; dasatinib; daunorubicin; degarelix; denileukin diftitox; dexrazoxane; docetaxel; doxorubicin; dromostanolone propionate; eculizumab; Elliott's B Solution; eltrombopag; epirubicin; epoetin alfa; erlotinib; estramustine; etoposide phosphate; etoposide; everolimus; exemestane; filgrastim; floxuridine; fludarabine; fluorouracil; fulvestrant; gefitinib; gemcitabine; gemtuzumab ozogamicin; goserelin acetate; histrelin acetate; hydroxyurea; ibritumomab tiuxetan; idarubicin; ifosfamide; imatinib mesylate; interferon alfa 2a; interferon alfa-2b; irinotecan; ixabepilone; lapatinib; lenalidomide; letrozole; leucovorin; leuprolide acetate; levamisole; lomustine; meclorethamine, nitrogen mustard; megestrol acetate; melphalan, L-PAM; mercaptopurine; mesna; methotrexate; methoxsalen; mitomycin C; mitotane; mitoxantrone; nandrolone phenpropionate; nelarabine; nilotinib; Nofetumomab; ofatumumab; oprelvekin; oxaliplatin; paclitaxel; palifermin; pamidronat; panitumumab; pazopanib; pegademase; pegaspargase; Pegfilgrastim; pemetrexed disodium; pentostatin; pipobroman; plerixafor; plicamycin, mithramycin); porfimer sodium; pralatrexate; procarbazine; quinacrine; Rasburicase; raloxifene hydrochloride; Rituximab; romidepsin; romiplostim; sargramostim; sargramostim; satraplatin; sorafenib; streptozocin; sunitinib maleate; tamoxifen; temozolomide; temsirolimus; teniposide; testolactone; thioguanine; thiotepa; topotecan; toremifene; tositumomab; trastuzumab; tretinoin; uracil mustard; valrubicin; vinblastine; vincristine; vinorelbine; vorinostat; and zoledronate.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates, to optimise the activity and/or stability and/or physical characteristics, such as solubility, of the therapeutic ingredient. It will be clear also that, where appropriate, the therapeutic ingredients may be used in optically pure form.

The combinations referred to above may conveniently be presented for use in the form of a pharmaceutical composition and thus pharmaceutical compositions comprising a combination as defined above together with a pharmaceutically acceptable diluent or carrier represent a further aspect of the invention. These combinations are of particular interest in respiratory diseases and are conveniently adapted for inhaled or intranasal delivery.

The individual compounds of such combinations may be administered either sequentially or simultaneously in separate or combined pharmaceutical compositions. Preferably, the individual compounds will be administered simultaneously in a combined pharmaceutical composition. Appropriate doses of known therapeutic agents will be readily appreciated by those skilled in the art.

General Synthesis

The compounds of the present invention can be prepared by methods well known in the art of organic chemistry. See, for example, J. March, 'Advanced Organic Chemistry' 4$^{th}$ Edition, John Wiley and Sons. During synthetic sequences it may be necessary and/or desirable to protect sensitive or reactive groups on any of the molecules concerned. This is achieved by means of conventional protecting groups, such as those described in T. W. Greene and P. G. M. Wutts 'Protective Groups in Organic Synthesis' 3$^{rd}$ Edition, John Wiley and Sons, 1999. The protective groups are optionally removed at a convenient subsequent stage using methods well known in the art.

The products of the reactions are optionally isolated and purified, if desired, using conventional techniques, but not limited to, filtration, distillation, crystallization, chromatography and the like. Such materials are optionally characterized using conventional means, including physical constants and spectral data. The 1H-pyrazolo[3,4-c]pyridin-7-amine derivatives of the present invention can be prepared by methods well known in the art of organic chemistry. See, for example, J. March, 'Advanced Organic Chemistry' 4$^{th}$ Edition, John Wiley and Sons. During synthetic sequences it may be necessary and/or desirable to protect sensitive or reactive groups on any of the molecules concerned. This is achieved by means of conventional protecting groups, such as those described in T. W. Greene and P. G. M. Wutts 'Protective Groups in Organic Synthesis' 3$^{rd}$ Edition, John Wiley and Sons, 1999. The protective groups are optionally removed at a convenient subsequent stage using methods well known in the art.

The products of the reactions are optionally isolated and purified, if desired, using conventional techniques, but not limited to, filtration, distillation, crystallization, chromatography and the like. Such materials are optionally characterized using conventional means, including physical constants and spectral data.

Scheme I

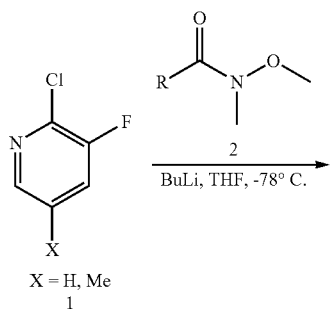

X = H, Me
1

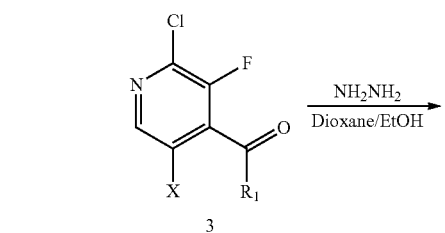

3

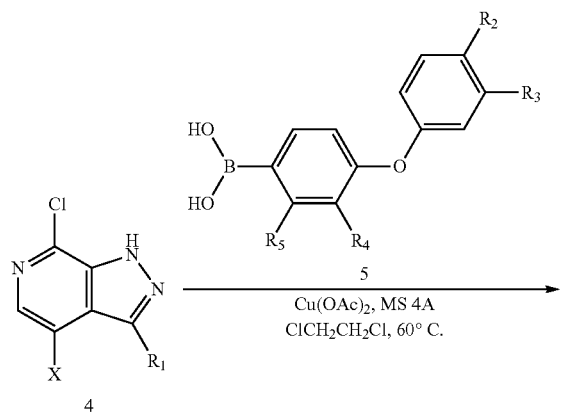

4

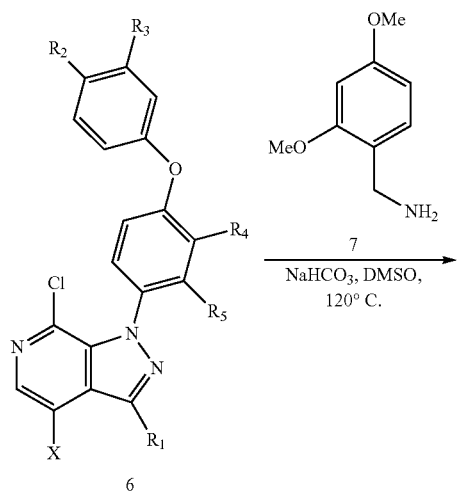

6

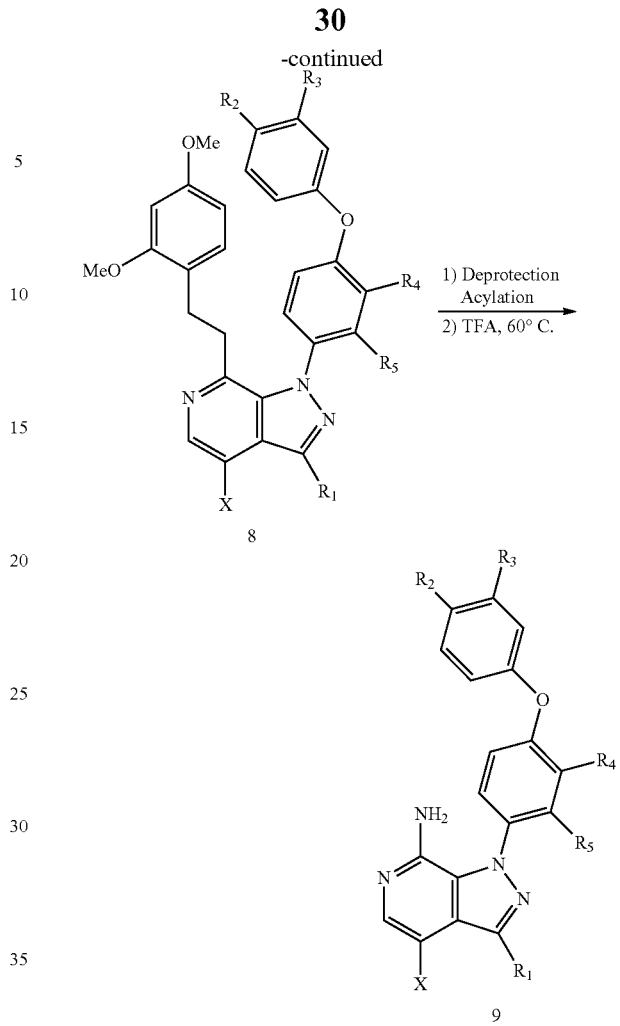

Scheme 1 shows one of the route to prepare this series compounds with a 1H-pyrazolo[3,4-c]pyridin-7-amine core. The synthesis starts from the commercially available 2-chloro3-fluoropyridine 1 by reacting with Weinreib's amide after treatment with butyl lithium in THF at low temperature to afford 4-acyl 2-chloro-3-fluoropyridine 2. The cyclization of the ketone with hydrazine in dioxane/EtOH under heating forms the pyrzaolopyridine core 4. The arylation of the pyrazole nitrogen with biarylether boronic acid 5 generates compound 6. Then the chloro on the 7-position can be replaced by 2,4-dimethoxybenzyl amine under heating with sodium bicarbonate in DMSO to compound 8. The functional group on the R1 substitution can be converted, such as deprotection and acylation before the removal of the dimethoxybenzyl group on the 7-amino to provide the final BTK inhibitor compound 9.

The present invention also includes within its scope all stereoisomeric forms of the Btk inhibitor compounds according to the present invention resulting, for example, because of configurational or geometrical isomerism. Such stereoisomeric forms are enantiomers, diastereoisomers, cis and trans isomers etc. For example where azepane-2-carboxylic acid is used as amino acid, there exists a mixture of two enantiomers. In the case of the individual stereoisomers of compounds of Formula I or salts or solvates thereof, the present invention includes the aforementioned stereoisomers substantially free, i.e., associated with less than 5%, preferably less than 2% and in particular less than 1% of the other stereoisomer. Mixtures of stereoisomers in any proportion, for example a racemic mixture comprising substantially equal amounts of two enantiomers are also included within the scope of the present invention.

For chiral compounds, methods for asymmetric synthesis whereby the pure stereoisomers are obtained are well known in the art, e.g. synthesis with chiral induction, synthesis starting from chiral intermediates, enantioselective enzymatic conversions, separation of stereoisomers using chromatography on chiral media. Such methods are described in *Chirality in Industry* (edited by A. N. Collins, G. N. Sheldrake and J. Crosby, 1992; John Wiley). Likewise methods for synthesis of geometrical isomers are also well known in the art.

The Btk inhibitor compounds of the present invention, which can be in the form of a free base, may be isolated from the reaction mixture in the form of a pharmaceutically acceptable salt. The pharmaceutically acceptable salts may also be obtained by treating the free base of Formula I with an organic or inorganic acid such as hydrogen chloride, hydrogen bromide, hydrogen iodide, sulfuric acid, phosphoric acid, acetic acid, propionic acid, glycolic acid, maleic acid, malonic acid, methanesulphonic acid, fumaric acid, succinic acid, tartaric acid, citric acid, benzoic acid, and ascorbic acid.

The Btk inhibitor compounds of the present invention also exist as amorphous forms. Multiple crystalline forms are also possible. All the physical forms are included within the scope of the present invention.

Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.* 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example IR spectroscopy, show the presence of the solvent (or water) in the crystals as a solvate (or hydrate).

The invention is illustrated by the following examples.

EXAMPLES

The following examples are illustrative embodiments of the invention, not limiting the scope of the invention in any way. Reagents are commercially available or are prepared according to procedures in the literature.

Mass Spectrometry: Electron Spray spectra were recorded on the Applied Biosystems API-165 single quad mass spectrometer in alternating positive and negative ion mode using Flow Injection. The mass range was 120-2000 Da and scanned with a step rate of 0.2 Da. and the capillary voltage was set to 5000 V. $N_2$-gas was used for nebulisation.

LC-MS spectrometer (Waters) Detector: PDA (200-320 nm), Mass detector: ZQ and Eluent: A: acetonitrile with 0.05% trifluoroacetic acid, B: acetonitrile/water=1/9 (v/v) with 0.05% trifluoroacetic acid.

Method LCMS (A)

| Column | Agilent TC-C18, 50 × 2.1 mm, 5 μm |
|---|---|
| Mobile Phase | A: $H_2O$ (0.1% TFA) |
| | B: $CH_3CN$ (0.05% TFA) |
| | Stop Time: 4.5 min |

| | Time (min) | B % |
|---|---|---|
| Gradient | 0 | 1 |
| | 0.4 | 1 |
| | 3.4 | 90 |
| | 3.9 | 100 |
| | 3.91 | 1 |

| Sample injection volume | 2 μl |
|---|---|
| Flow Rate | 0.8 ml/min |
| Wavelength | 220 nm |
| Oven Tem. | 50° C. |
| MS polarity | ESI POS |

Method B: LC-MS

| Column | Agilent TC-C18, 50 × 2.1 mm, 5 μm |
|---|---|
| Mobile Phase | A: $H_2O$ (0.1% TFA) |
| | B: MeCN (0.05% TFA) |
| | Stop Time: 4.5 min |

| | Time (min) | B % |
|---|---|---|
| Gradient | 0 | 1 |
| | 0.4 | 1 |
| | 3.4 | 90 |
| | 3.9 | 100 |
| | 3.91 | 1 |

| Sample injection volume | 2 μl |
|---|---|
| Flow Rate | 0.8 ml/min |
| Wavelength | 220 nm |
| Oven Temp. | 50° C. |
| MS polarity | ESI POS |

Method C:
Sample Info: Easy-Access Method: '1-Short_TFA_Pos'
Method Info: B222 Column Agilent SBC (3.0×50 mm, 1.8μ); Flow 1.0 mL/min;
solvent A: $H_2O$-0.1% TFA;
solvent B: MeCN-0.1% TFA;
GRADIENT TABLE: 0 min:10% B, 0.3 min:10% B, 1.5 min:95% B, 2.70 min:95% B, 2.76 min:10% B
stop time 3.60 min, PostTime 0.70 min.
Method D:
Sample Info: Easy-Access Method: '1_Fast'
  Method Info: A330 Column Agilent Zorbax SB-C18 (2.1×30 mm, 3.5μ); Flow 2.0 mL/min;
solvent A: $H_2O$-0.1% TFA;
solvent B: MeCN-0.1% TFA;
GRADIENT TABLE: 0.01 min:10% B, 1.01 min:95% B, 1.37 min:95% B, 1.38 min:10% B, stop time 1.7 min, PostTime=OFF
Method E:
Mobile Phase: 0.1% TFA in MeCN and 0.1% TFA in Water
Column: Xterra 2.1×20 mm 3.5 μm IS or SunFire
Flow rate=1.5 mL/min
Injection Volume=5 μL
Column Heater=50° C.
Run time=4 min
Flow rate=1.5 mL/min
Injection Volume=5 μL Gradient:

| Time | % A | % B |
| --- | --- | --- |
| 0.00 | 95 | 5 |
| 3.00 | 5 | 95 |
| 3.25 | 2 | 98 |
| 3.26 | 95 | 5 |

Method F:
Mobile Phase: A: 0.1% TFA in MeCN and B: 0.1% TFA in Water
Column: Xterra 2.1×20 mm 3.5 μm IS or SunFire
Flow rate=1.5 mL/min
Injection Volume=5 μL
Column Heater=50° C.
Run time=2 min
Flow rate=1.5 mL/min
Injection Volume=5 μL
Gradient:

| Time | % A | % B |
| --- | --- | --- |
| 0.00 | 95 | 5 |
| .75 | 5 | 95 |
| 1.25 | 2 | 98 |
| 1.26 | 95 | 5 |

Method G:
Acquity UPLC BEH-C18, 1.7 μm, 2.1×50 mm
1 mL/min flow
5%-100% MeCN in 1.4 min
0.1% $NH_3$
Preparative HPLC was conducted on a column (50×10 mm ID, 5 μm, Xterra Prep MS C18) at a flow rate of 5 ml/min, injection volume 500 μl, at room temperature and UV Detection at 210 nm.

The following abbreviations are used throughout the application with respect to chemical terminology:
HATU O-(7-Azabenzotriazol-1-yl)-1,1,3,3-tetramethyluroniumhexafluoro phosphate
Cbz Benzyloxycarbonyl
D Deuterated Hydrogen
DMF N,N-Dimethylformamide
DCM Dichloromethane
EtOAc Ethyl acetate
DIPEA N,N-Diisopropylethylamine
THF Tetrahydrofuran
EtOH Ethanol
EDCI.HCl 1-(3-Dimethylaminopropyl)-3-ethylcarbodiimide. hydrochloride
4-DMAP 4-Dimethylamino pyridine
PyBOP O-Benzotriazole-1-yl-oxy-trispyrrolidinophosphonium hexafluorophosphate
TBTU O-Benzotriazol-1-yl-N,N,N',N'-tetramethyluronium tetrafluoroborate
HBr Hydrogen bromide
HCl Hydrogen chloride
HOAc Acetic acid
$POCl_3$ Phosphorous oxychloride
HPLC High Pressure Liquid Chromatography
UPLC Ultra Performance Liquid Chromatography
LiHMDS Lithium hexamethyldisilazide
MeOH Methanol
DCM Dichloromethane
n-BuLi n-Butyllithium
$CO_2$ Carbondioxide
$NaHCO_3$ Sodiumbicarbonate
$K_3PO_4$ Potassium phosphate
$P(Cy)_3$ Tricyclohexylphosphine
$Pd(OAc)_2$ Palladium(II) acetate
$Na_2SO_4$ Sodium sulfate
$Na_2CO_3$ Sodium carbonate
DAST Diethylaminosulfur trifluoride
$Cs_2CO_3$ Cesium carbonate
$Et_2O$ Diethylether
$Na_2S_2O_3$ Sodium thiosulfate
$Na_2S_2O_4$ Sodium hydrosulfite
$NaCNBH_3$ Sodium cyanoborohydride
$NH_4Cl$ Ammonium chloride
$MgSO_4$ Magnesium sulfate
LiOH Lithium hydroxide
IPA Isopropylamine
TFA Trifluoro acetic acid
Cbz-Cl Benzylchloroformate
PE Petroleum ether
EA Ethyl acetate
NaHMDS Sodium hexamethyldisilazide
10% Pd/C 10% Palladium on carbon
TEA Triethyl amine
CDI 1,1'-Carbonyl diimidazole
DMI 1,3-Dimethyl-2-imidazolidinone
NBS N-Bromosuccinimide
i-PrOH 2-Propanol
$K_2CO_3$ Potassium carbonate
$Pd(dppf)Cl_2$ 1,1'-Bis(diphenylphosphino)ferrocene palladium (II) chloride, complex with dichloromethane
$Et_3N$ Triethylamine
2-BuOH 2-Butanol
LCMS Liquid Chromatography/Mass Spectrometry
MeCN Acetonitril
$NH_3$ Ammonia
$CD_3I$ Trideuteromethyl iodide
$CD_3OD$ Tetradeuteromethanol
$CH_3I$ Iodomethane
$CBr_4$ Carbon tetrabromide
Tris-HCl Tris(hydroxymethyl)aminomethane.hydrochloride
$MgCl_2$ Magnesium chloride
$NaN_3$ Sodium azide
DTT Dithiothreitol
DMSO Dimethyl sulfoxide
IMAP Immobilized Metal Ion Affinity-Based Fluorescence Polarization
ATP Adenosine triphosphate
$MnCl_2$ Manganese(II)chloride
DMA Dimethylacetamide
IPA Isopropyl alcohol
TPP triphenylphosphine
DIAD Diisopropyl azodicarboxylate
DMB 2,4-dimethoxybenzyl
DCE Dichloroethane
DEAD Diethyl azodicarboxylate
ACN Acetonitrile
RT (rt) Room Temperature
Aq Aqueous
EtOH Ethanol
MPLC Medium Pressure Liquid Chromoatography
Xantphos 4,5-Bis(diphenylphosphino)-9,9-dimethylxanthene
X-phos 2-Dicyclohexylphosphino-2',4',6'-triisopropylbiphenyl
TFA trifluoroacetic acid

Intermediate 1

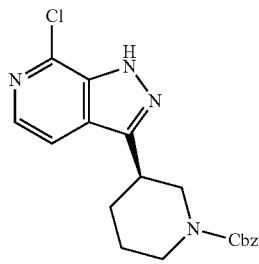 [SMILES: O=C(OCc1ccccc1)N1CCC[C@@H](c2n[nH]c3c(Cl)nccc23)C1]

(R)-benzyl 3-(7-chloro-1H-pyrazolo[3,4-c]pyridin-3-yl)piperidine-1-carboxylate

Step 1: (R)-benzyl 3-(methoxy(methyl)carbamoyl)piperidine-1-carboxylate

To a 500 ml one necked round bottom flask was charged with N,O-deimethylhydroxylamine hydrochloride (6.55 g, 67.1 mmol), CH2Cl2 (10 ml), Hunig's Base (10.31 g, 89 mmol) and (R)-1-((benzyloxy)carbonyl)piperidine-3-carboxylic acid (11.780 g, 44.7 mmol). The mixture was stirred and then propylphosphoric cyclic anhydride (42.7 g, 134 mmol) was added. The resulting reaction mixture was then stirred at room temperature for 18 hrs overnight. LC-MS showed complete conversion of starting material to product. The reaction was quenched by addition of water (3 mL) and stirred at room temperature for 10 min. Then the mixture was partitioned between NaHCO$_3$ (sat, 30 mL) and ethyl acetate (50 mL). The organic layer were separated and the aqueous layer was extracted by ethyl acetate (2×50 ML). The combined organic phases were washed with water (30 ML), brine, dried over MgSO4, filtered and concentrated. The crude was purified by MPLC (40 g silica gel, 30 to 100% ethyl acetate in hexanes 18 CV) to afford colorless stick oil (R)-benzyl 3-(methoxy(methyl)carbamoyl)piperidine-1-carboxylate. LC-MS: C16H22N2O4. found [M+H]+: 307.2, RT=1.62 min. 1H NMR (500 Hz, CDCl$_3$, δ):7.30-7.35 (5H, m), 5.13 (2H, dd, J=12.4 Hz), 4.21 (2H, br), 3.59-3.72 (3H, br), 3.16 (3H, s), 2.75-2.95 (4H, br), 1.94 (1H, d, J=12.6 Hz), 1.64-1.75 (2H, m), 1.56 (1H, br) ppm.

Step 2: (R)-benzyl 3-(2-chloro-3-fluoroisonicotinoyl)piperidine-1-carboxylate To a 100 ml one neck round bottom flask was charged with 2-chloro-3-fluoropyridine (1288 mg, 9.79 mmol) and THF (15 mL). The mixture was cooled to −78° C. and then a solution of n-butyl lithium (0.914 ml, 9.14 mmol) in THF was added dropwise. The mixture was aged at −78° C. for 1 hr, and a solution of (R)-benzyl 3-(methoxy(methyl)carbamoyl)piperidine-1-carboxylate (2000 mg, 6.53 mmol) in THF (15 mL) was added dropwise by syringe. The resulting reaction mixture was stirred at −78° C. for 2 hrs. LC-MS showed complete consumption of starting material and formation of product. The reaction was quenched by addition of NH4Cl (sat, 5 mL), diluted with ethyl acetate (20 mL) and water (5 mL). The organic layer was separated and the aqueous layer was extracted by ethyl acetate (3×10 mL). The combined organic phases were washed with brine, dried over MgSO4, filtered and concentrated. The crude was purified by MPLC (120 g silica gel, 10 to 40% ethyl acetate in hexanes, 28 CV) to afford sticky oil (R)-benzyl 3-(2-chloro-3-fluoroisonicotinoyl)piperidine-1-carboxylate. LC-MS: C19H18ClFN2O3. found [M+H]+: 377.1, RT=2.00 min. 1H NMR (500 Hz, CDCl$_3$, δ): 8.29 (1H, s), 7.45 (1H,$), 7.33 (5H, m), 5.12 (2H, m), 4.24 (1H, m), 4.00 (1H, d, J=12 Hz), 3.17 (2H, m), 3.00 (1H, td, J=11.0, 2.6 Hz), 2.04, 1H, m), 1.80 (1H, m), 1.55-1.70 (3H, m) ppm.

Step 3: (R)-benzyl 3-(7-chloro-1H-pyrazolo[3,4-c]pyridin-3-yl)piperidine-1-carboxylate To a 20 ml sample vial was charged with (R)-benzyl 3-(2-chloro-3-fluoroisonicotinoyl)piperidine-1-carboxylate (1910 mg, 5.07 mmol) along sodium bicarbonate (426 mg, 5.07 mmol), Dioxane (15 ml) and Ethanol (3 ml). Hydrazine (179 mg, 5.58 mmol) was added dropwise vial a syringe. The mixture was then stirred and heated in an oil bath of 70° C. for 15 hrs overnight. The reaction mixture was then concentrated and the crude was purified by MPLC (80 g silica gel, 15 to 50% ethyl acetate in hexanes, 28 CV) to afford product (R)-benzyl 3-(7-chloro-1H-pyrazolo[3,4-c]pyridin-3-yl)piperidine-1-carboxylate. LC-MS: Cl9H19ClN4O2. found [M+H]+: 371.1, RT=1.19 min. 1H NMR (500 Hz, CDCl$_3$, δ): 10.57 (1H, m), 8.05 (1H, s), 7.33-7.58 (5H, m), 5.17 (2H, s), 4.50 (1H, d, J=16 Hz), 4.39 (1H, m), 3.11-3.20 (2H, m), 2.96 (1H, t, J=12 Hz), 2.23 (1H, d, J=13.2 Hz), 1.87-1.95 (2H, m), 1.69 (1H, m) ppm.

Intermediate 2

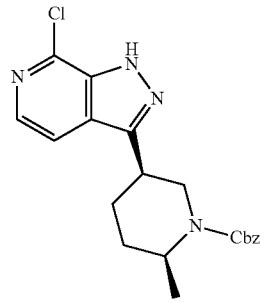 [SMILES: C[C@H]1CC[C@@H](c2n[nH]c3c(Cl)nccc23)CN1C(=O)OCc1ccccc1]

(2S,5R)-benzyl 5-(7-chloro-1H-pyrazolo[3,4-c]pyridin-3-yl)-2-methylpiperidine-1-carboxylate

Step 1: (2S,5R)-benzyl 5-(2-chloro-3-fluoroisonicotinoyl)-2-methylpiperidine-1-carboxylate To a flask was charged with 2-chloro-3-fluoropyridine (0.622 ml, 6.24 mmol) and THF (15 mL). The mixture was cooled to −78° C. and then a solution of n-butyl lithium BuLi (1.873 ml, 4.68 mmol) in THF was added dropwise. The mixture was aged at −78° C. for 30 min, and a solution of (2S,5R)-benzyl 5-(methoxy(methyl)carbamoyl)-2-methylpiperidine-1-carboxylate (1.0 g, 3.12 mmol) in THF (15 mL) was added dropwise by syringe. The resulting reaction mixture was stirred at −78° C. for 2 hrs. The mixture was quenched with water at low temperature, extracted with EtOAc 3×, dried over MgSO4, filtered and concentrated in vacuo. Crude was loaded and purified on 24 gr Redi Sep Rf filter column on CombiFlash with 0-40% Hexane/EtOAc solvent system to provide product (2S,5R)-benzyl 5-(2- chloro-3-fluoroisonicotinoyl)-2-methylpiperidine-1-carboxylate LC-MS (ES, m/z) $C_{20}H_{20}ClFN_2O_3$: 390. Found 391 [M+H]$^+$.

Step 2: (2S,5R)-benzyl 5-(7-chloro-1H-pyrazolo[3,4-c]pyridin-3-yl)-2-methylpiperidine-1-carboxylate To a seal tube was charged with (2S,5R)-benzyl 5-(2-chloro-3-fluoroisonicotinoyl)-2-methylpiperidine-1-carboxylate (1.212 g, 3.10 mmol) along with SODIUM BICARBONATE (0.261 g, 3.10 mmol), Dioxane (20.0 ml) and Ethanol (7.0 ml). HYDRAZINE (0.109 ml, 3.41 mmol) was then added dropwise via a syringe. The mixture was then stirred and heated in an oil bath at 70° C. for 15 hrs overnight. The reaction mixture was then concentrated and the crude was purified by MPLC (40 g silica gel, 0 to 30% ethyl acetate in hexanes) to afford product (2S,5R)-benzyl 5-(7-chloro-1H-pyrazolo[3,4-c]pyridin-3-yl)-2-methylpiperidine-1-carboxylate LC-MS (ES, m/z) $C_{20}H_{21}ClN_4O_2$: 384. Found 385[M+H]$^+$.

Intermediate 3

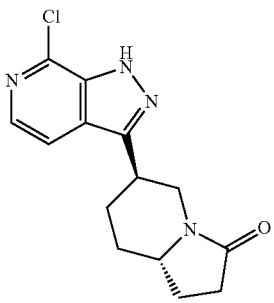 [SMILES: O=C1CC[C@@H]2CC[C@@H](c3n[nH]c4c(Cl)nccc34)CN12]

(6R,8aS)-6-(7-chloro-1H-pyrazolo[3,4-c]pyridin-3-yl)hexahydroindolizin-3(2H)-one Step 1: (6R,8aS)-N-methoxy-N-methyl-3-oxooctahydroindolizine-6-carboxamide To a 100 ml flask was charged with N,O-DIMETHYLHYDROXYLAMINE HYDROCHLORIDE (1.597 g, 16.38 mmol), $CH_2Cl_2$ (40 ml), Hunig's Base (3.81 ml, 21.83 mmol) and (6R,8aS)-3-oxooctahydroindolizine-6-carboxylic acid (2.0 g, 10.92 mmol). The mixture was stirred and then 2,4,6-tripropyl-1,3,5,2,4,6-trioxatriphosphinane 2,4,6-trioxide (19.12 ml, 32.8 mmol) was added. The resulting reaction mixture was then stirred at room temperature for 18 hrs overnight. The reaction was quenched by addition of water and stirred at room temperature for 7 min. Then the mixture was partitioned between sat.NaHCO3 and EtOAc, the organic layer was separated washed with water and the aqueous layer was extracted with EOAc 2x, DCM 2x, 7% MeOHin DCM2x. Organics were dried over MgSO4, filtered and concentrated in vacuo to give crude. Crude was loaded and purified on 80 gr Redi Sep Rf filter column on CombiFlash with 10% MeOH/DCM 0-4%. Appropriate fractions collected and concetrated in vacuo to afford (6R,8aS)-N-methoxy-N-methyl-3-oxooctahydroindolizine-6-carboxamide LC-MS (ES, m/z) $C_{11}H_8N_2O_3$: 226. Found 227[M+H]$^+$.

Step 2: (6R,8aS)-6-(2-chloro-3-fluoroisonicotinoyl)hexahydroindolizin-3(2H)-one

To a flask was charged with 2-chloro-3-fluoropyridine (1.163 g, 8.84 mmol) and THF (15 mL). The mixture was cooled to –78° C. and then a solution of n-butyl lithium BuLi (2.83 ml, 7.07 mmol) in toluene solution was added dropwise. The mixture was aged at –78° C. for 30 min, and a solution of (6R,8aS)-N-methoxy-N-methyl-3-oxooctahydroindolizine-6-carboxamide (1.0 g, 4.42 mmol) in THF (2.5 mL) was added dropwise by syringe. The resulting reaction mixture was stirred at –78° C. for 2 hrs. The mixture was quenched with water at low temperature, extracted with EtOAc 3x, dried over MgSO4, filtered and concentrated in vacuo to give crude. Crude was loaded and purified on 24 gr Redi Sep Rf filter column on CombiFlash with 10% MeOH/DCM 0-3% to afford product (6R,8aS)-6-(2-chloro-3-fluoroisonicotinoyl)hexahydroindolizin-3(2H)-one LC-MS (ES, m/z) $C_{14}H_{14}ClFN_2O_2$: 296. Found 297 [M+H]$^+$.

Step 3: (6R,8aS)-6-(7-chloro-1H-pyrazolo[3,4-c]pyridin-3-yl)hexahydroindolizin-3(2H)-one To a 20 ml seal tube was charged with (6R,8aS)-6-(2-chloro-3-fluoroisonicotinoyl)hexahydroindolizin-3(2H)-one (0.538 g, 1.813 mmol) along with SODIUM BICARBONATE (0.152 g, 1.813 mmol), 1,4-Dioxane (12.5 ml) and Ethanol (4.5 ml). HYDRAZINE (0.064 ml, 1.994 mmol) was then added dropwise vial a syringe. The mixture was then stirred and heated in an oil bath of 70° C. for 15 hrs overnight. The reaction mixture was then concentrated and the crude was purified by MPLC 24 gr Redi Sep Rf filter column on CombiFlash with 10% MeOH/DCM 0-5% to afford product (6R,8aS)-6-(7-chloro-1H-pyrazolo[3,4-c]pyridin-3-yl)hexahydroindolizin-3(2H)-one LC-MS (ES, m/z) $C_{14}H_{15}ClN_4O$: 290. Found 291 [M+H]$^+$.

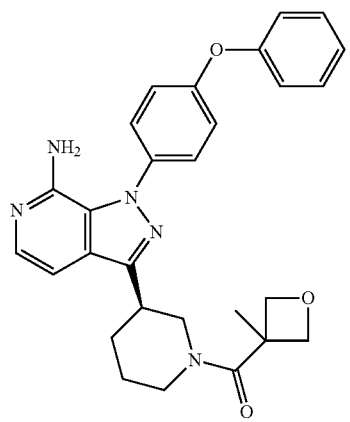 [SMILES: CC1(C(=O)N2CCC[C@@H](c3nn(-c4ccc(Oc5ccccc5)cc4)c4c(N)nccc34)C2)COC1]

Example 1

(R)-(3-(7-amino-1-(4-phenoxyphenyl)-1H-pyrazolo[3,4-c]pyridin-3-yl)piperidin-1-yl)(3-methyloxetan-3-yl)methanone Step 1: (R)-benzyl 3-(7-chloro-1-(4-phenoxyphenyl)-1H-pyrazolo[3,4-c]pyridin-3-yl)piperidine-1-carboxylate To a flask was charged with (4-phenoxyphenyl)boronic acid (4.62 g, 21.57 mmol), (R)-benzyl 3-(7-chloro-1H- pyrazolo[3,4-c]pyridin-3-yl)piperidine-1-carboxylate (5.0 g, 13.48 mmol), COPPER (II) ACETATE (3.92 g, 21.57 mmol), pyridine (2.181 ml, 27.0 mmol), stirred in ClCH$_2$CH$_2$Cl (100 ml) and 4A MS 5000 mg. The resulting mixture was stirred at 60° C. overnight under air. Reaction was stopped, mixture filtered and washed with EtOAc. The filtrate concentrated in vacuo to give crude. Crude was purified on 80 g Redi Sep Rf filter column on CombiFlash with 0-35% Hex/EtOAc to afford product (R)-benzyl 3-(7-chloro-1-(4-phenoxyphenyl)-1H-pyrazolo[3,4-c]pyridin-3-yl)piperidine-1-carboxylate LC-MS (ES, m/z) C$_{31}$H$_{27}$ClN$_4$O$_3$: 539. Found 539 [M+H]$^+$.

Step 2: (R)-benzyl 3-(7-((2,4-dimethoxybenzyl)amino)-1-(4-phenoxyphenyl)-1H-pyrazolo[3,4-c]pyridin-3-yl)piperidine-1-carboxylate To a seal tube was charged with (R)-benzyl 3-(7-chloro-1-(4-phenoxyphenyl)-1H-pyrazolo[3,4-c]pyridin-3-yl)piperidine-1-carboxylate (5.88 g, 10.91 mmol), (2,4-dimethoxyphenyl)methanamine (18.24 g, 109 mmol) and sodium bicarbonate (1.833 g, 21.82 mmol) were stirred at 130° C. overnight. The mixture was diluted with water and extracted with EtOAc (3×). The combined organic phases were dried over MgSO$_4$, filtered and concentrated in vacuo to give crude. The crude was purified on 80 g column ISCO RediSep system 0-35% Hex/EtOAc to afford product (R)-benzyl 3-(7-((2,4-dimethoxybenzyl)amino)-1-(4-phenoxyphenyl)-1H-pyrazolo[3,4-c]pyridin-3-yl)piperidine-1-carboxylate LC-MS (ES, m/z) C$_{40}$H$_{39}$N$_5$O$_5$: 669. Found 670 [M+H]$^+$.

Step 3: (R)-N-(2,4-dimethoxybenzyl)-1-(4-phenoxyphenyl)-3-(piperidin-3-yl)-1H-pyrazolo[3,4-c]pyridin-7-amine In hydrogenation vessel was added (R)-benzyl 3-(7-((2,4-dimethoxybenzyl)amino)-1-(4-phenoxyphenyl)-1H-pyrazolo[3,4-c]pyridin-3-yl)piperidine-1-carboxylate (3.36 g, 5.02 mmol), Pd(OH)$_2$ (3.52 g, 5.02 mmol) dissolved in Methanol (40 ml). The resulting mixture was degassed and hydrogenated at 50 psi overnight. The mixture was filtered and the solvent was concentrated in vacuo to afford product (R)-N-(2,4-dimethoxybenzyl)-1-(4-phenoxyphenyl)-3-(piperidin-3-yl)-1H-pyrazolo[3,4-c]pyridin-7-amine LC-MS (ES, m/z) C$_{32}$H$_{33}$N$_5$O$_3$: 535. Found 536 [M+H]$^+$.

Step 4: (R)-(3-(7-((2,4-dimethoxybenzyl)amino)-1-(4-phenoxyphenyl)-1H-pyrazolo[3,4-c]pyridin-3-yl)piperidin-1-yl)(3-methyloxetan-3-yl)methanone To a 20 ml vial was added 3-methyloxetane-3-carboxylic acid (7.59 mg, 0.065 mmol), DIEA (0.034 ml, 0.196 mmol), HATU (0.030 g, 0.078 mmol) stirred in DMF 1.0 mL. The resulting mixture was stirred for 10 min followed by dropwise addition to solution of (R)-N-(2,4-dimethoxybenzyl)-1-(4-phenoxyphenyl)-3-(piperidin-3-yl)-1H-pyrazolo[3,4-c]pyridin-7-amine (0.035 g, 0.065 mmol) in DMF (1 mL). The resulting mixture was stirred at room temperature for 3 h. Mixture was diluted with EtOAc and 3 mL sat. NaHCO$_3$ added, organic layer separated, dried over MgSO$_4$ and concetrated in vacuo. The crude was purified on 4 gr Redi Sep Rf filter column on CombiFlash with Hex/EtOAc 0-70% to give product (R)-(3-(7-((2,4-dimethoxybenzyl)amino)-1-(4-phenoxyphenyl)-1H-pyrazolo[3,4-c]pyridin-3-yl)piperidin-1-yl)(3-methyloxetan-3-yl)methanone.
LC-MS: C$_{37}$H$_{39}$N$_5$O$_5$. found [M+H]$^+$ 634.5, RT=1.34 min.

Step 5: (R)-(3-(7-amino-1-(4-phenoxyphenyl)-1H-pyrazolo[3,4-c]pyridin-3-yl)piperidin-1-yl)(3-methyloxetan-3-yl)methanone To a 25 ml flask was added (R)-(3-(7-(2,4-dimethoxybenzyl)amino)-1-(4-phenoxyphenyl)-1H-pyrazolo[3,4-c]pyridin-3-yl)piperidin-1-yl)(3-methyloxetan-3-yl)methanone, dissolved in TFA (3.0 mL, 38.9 mmol) and few drops of water. The resulting mixture was stirred at 80° C. for 2 h. Solvent was concentrated in vacuo and crude was purified on 4 gr Redi Sep Rf filter column on CombiFlash with 10% NH$_3$ 7N in methanol in DCM from 0-10% to afford (R)-(3-(7-amino-1-(4-phenoxyphenyl)-1H-pyrazolo[3,4-c]pyridin-3-yl)piperidin-1-yl)(3-methyloxetan-3-yl)methanone.
LC-MS: C$_{28}$H$_{29}$N$_5$O$_3$. found [M+H]+ 484.3, RT=1.21 min.

In the same procedure as Example 1, using different acid for the coupling in step 4, the following examples are prepared:

TABLE 1

| Example | Structure | IUPAC Name | Exact Mass [M + H]+ | Retention time (min) |
|---|---|---|---|---|
| Example 2 | 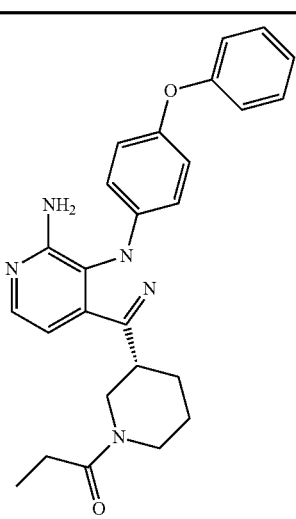 | 1-(4-phenoxyphenyl)-3-[(3R)-1-propanoylpiperidin-3-yl]-1H-pyrazolo[3,4-c]pyridin-7-amine | Calc'd 442.2, found 442.2 | 1.02 |

TABLE 1-continued

| Example | Structure | IUPAC Name | Exact Mass [M + H]+ | Retention time (min) |
| --- | --- | --- | --- | --- |
| Example 3 | 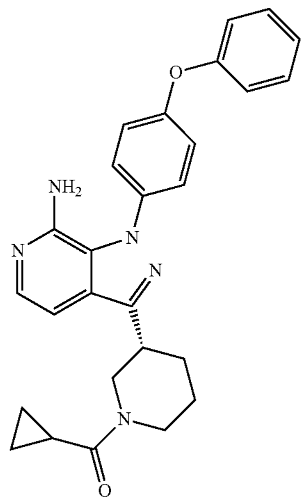 [SMILES: N=C(c1ccnc(N)c1Nc1ccc(Oc2ccccc2)cc1)[C@@H]1CCCN(C(=O)C2CC2)C1] | 3-[(3R)-1-(cyclopropylcarbonyl)piperidin-3-yl]-1-(4-phenoxyphenyl)-1H-pyrazolo[3,4-c]pyridin-7-amine | Calc'd 454.2, found 454.2 | 1.05 |
| Example 4 | 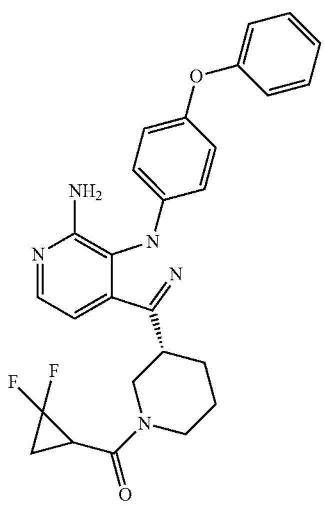 [SMILES: N=C(c1ccnc(N)c1Nc1ccc(Oc2ccccc2)cc1)[C@@H]1CCCN(C(=O)C2CC2(F)F)C1] | 3-{(3R)-1-[(2,2-difluorocyclopropyl)carbonyl]piperidin-3-yl}-1-(4-phenoxyphenyl)-1H-pyrazolo[3,4-c]pyridin-7-amine | Calc'd 490.2, found 490.2 | 1.08 |
| Example 5 | 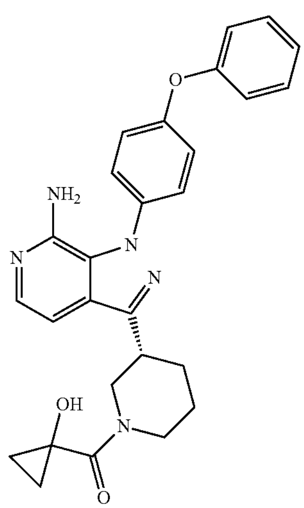 [SMILES: N=C(c1ccnc(N)c1Nc1ccc(Oc2ccccc2)cc1)[C@@H]1CCCN(C(=O)C2(O)CC2)C1] | 1-({(3R)-3-[7-amino-1-(4-phenoxyphenyl)-1H-pyrazolo[3,4-c]pyridin-3-yl]piperidin-1-yl}carbonyl)cyclopropanol | Calc'd 470.2, found 470.2 | 0.97 |

TABLE 1-continued

| Example | Structure | IUPAC Name | Exact Mass [M + H]+ | Retention time (min) |
|---|---|---|---|---|
| Example 6 | 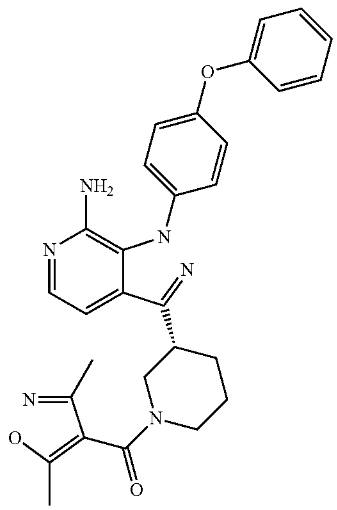 [SMILES: CC(=N)/C(C(=O)N1CCC[C@@H](C(=N)c2ccnc(N)c2Nc2ccc(Oc3ccccc3)cc2)C1)=C(/C)O] | 3-{(3R)-1-[(3,5-dimethylisoxazol-4-yl)carbonyl]piperidin-3-yl}-1-(4-phenoxyphenyl)-1H-pyrazolo[3,4-c]pyridin-7-amine | Calc'd 509.2, found 509.2 | 1.03 |
| Example 7 | 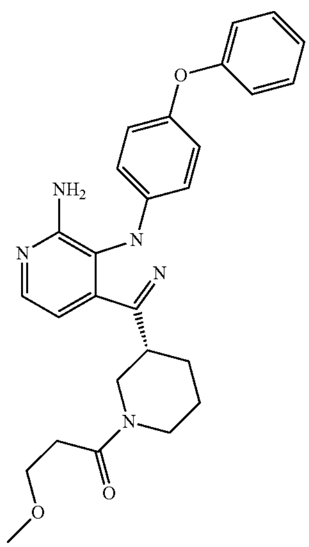 [SMILES: COCCC(=O)N1CCC[C@@H](C(=N)c2ccnc(N)c2Nc2ccc(Oc3ccccc3)cc2)C1] | 3-[(3R)-1-(3-methoxypropanoyl)piperidin-3-yl]-1-(4-phenoxyphenyl)-1H-pyrazolo[3,4-c]pyridin-7-amine | Calc'd 472.2, found 472.2 | 0.99 |
| Example 8 | 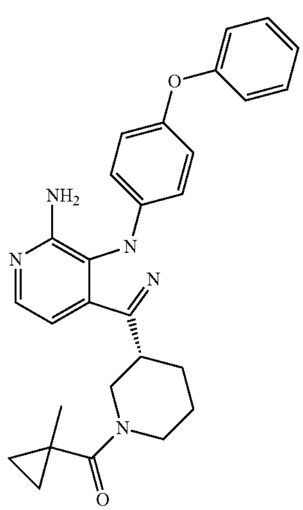 [SMILES: CC1(C(=O)N2CCC[C@@H](C(=N)c3ccnc(N)c3Nc3ccc(Oc4ccccc4)cc3)C2)CC1] | 3-{(3R)-1-[(1-methylcyclopropyl)carbonyl]piperidin-3-yl}-1-(4-phenoxyphenyl)-1H-pyrazolo[3,4-c]pyridin-7-amine | Calc'd 468.2, found 468.2 | 1.08 |

TABLE 1-continued

| Example | Structure | IUPAC Name | Exact Mass [M + H]+ | Retention time (min) |
|---|---|---|---|---|
| Example 9 | 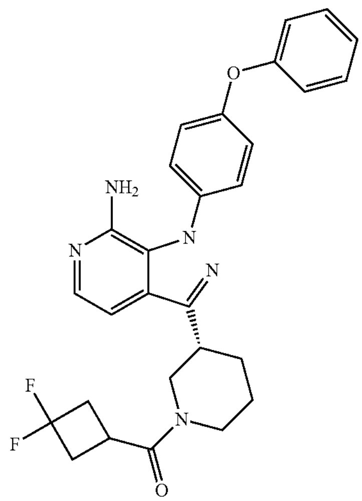 [SMILES: N=C(c1ccnc(N)c1Nc1ccc(Oc2ccccc2)cc1)[C@@H]1CCCN(C(=O)C2CC(F)(F)C2)C1] | 3-{(3R)-1-[(3,3-difluorocyclobutyl)carbonyl]piperidin-3-yl}-1-(4-phenoxyphenyl)-1H-pyrazolo[3,4-c]pyridin-7-amine | Calc'd 504.2, found 504.2 | 1.12 |
| Example 10 | 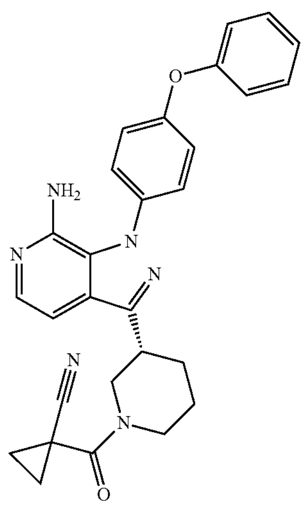 [SMILES: N#CC1(C(=O)N2CCC[C@@H](C(=N)c3ccnc(N)c3Nc3ccc(Oc4ccccc4)cc3)C2)CC1] | 1-({(3R)-3-[7-amino-1-(4-phenoxyphenyl)-1H-pyrazolo[3,4-c]pyridin-3-yl]piperidin-1-yl}carbonyl)cyclopropanecarbonitrile | Calc'd 479.2, found 479.2 | 1.04 |
| Example 11 | 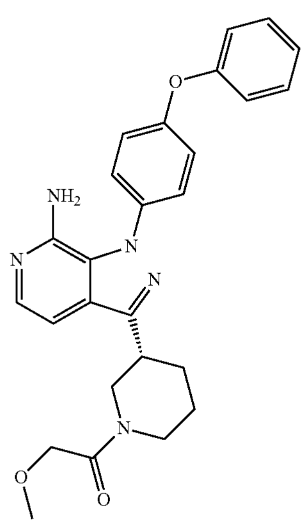 [SMILES: COCC(=O)N1CCC[C@@H](C(=N)c2ccnc(N)c2Nc2ccc(Oc3ccccc3)cc2)C1] | 3-[(3R)-1-(methoxyacetyl)piperidin-3-yl]-1-(4-phenoxyphenyl)-1H-pyrazolo[3,4-c]pyridin-7-amine | Calc'd 458.2, found 458.2 | 0.96 |

TABLE 1-continued

| Example | Structure | IUPAC Name | Exact Mass [M + H]+ | Retention time (min) |
|---|---|---|---|---|
| Example 12 | 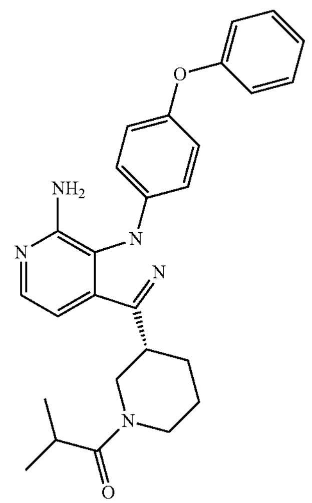 [SMILES: CC(C)C(=O)N1CCC[C@@H](C(=N)c2ccnc(N)c2Nc2ccc(Oc3ccccc3)cc2)C1] | 3-[(3R)-1-(2-methylpropanoyl)piperidin-3-yl]-1-(4-phenoxyphenyl)-1H-pyrazolo[3,4-c]pyridin-7-amine | Calc'd 456.2, found 456.2 | 1.09 |
| Example 13 | 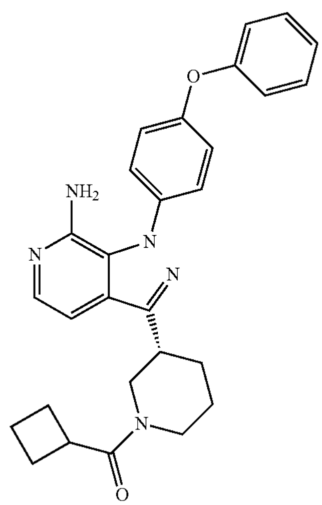 [SMILES: N=C(c1ccnc(N)c1Nc1ccc(Oc2ccccc2)cc1)[C@@H]1CCCN(C(=O)C2CCC2)C1] | 3-[(3R)-1-(cyclobutylcarbonyl)piperidin-3-yl]-1-(4-phenoxyphenyl)-1H-pyrazolo[3,4-c]pyridin-7-amine | Calc'd 468.2, found 468.2 | 1.13 |
| Example 14 | 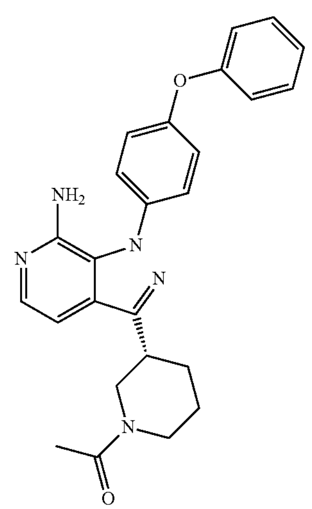 [SMILES: CC(=O)N1CCC[C@@H](C(=N)c2ccnc(N)c2Nc2ccc(Oc3ccccc3)cc2)C1] | 3-[(3R)-1-acetylpiperidin-3-yl]-1-(4-phenoxyphenyl)-1H-pyrazolo[3,4-c]pyridin-7-amine | Calc'd 428.2, found 428.2 | 0.95 |

TABLE 1-continued

| Example | Structure | IUPAC Name | Exact Mass [M + H]+ | Retention time (min) |
|---|---|---|---|---|
| Example 15 | 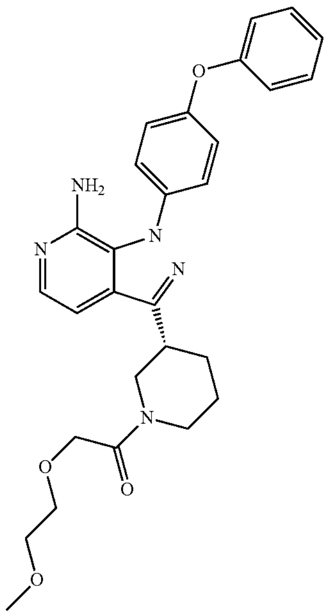 [SMILES: COCCOCC(=O)N1CCC[C@@H](C(=N)c2ccnc(N)c2Nc2ccc(Oc3ccccc3)cc2)C1] | 3-{(3R)-1-[(2-methoxyethoxy)acetyl]piperidin-3-yl}-1-(4-phenoxyphenyl)-1H-pyrazolo[3,4-c]pyridin-7-amine | Calc'd 502.2, found 502.2 | 0.97 |
| Example 16 | 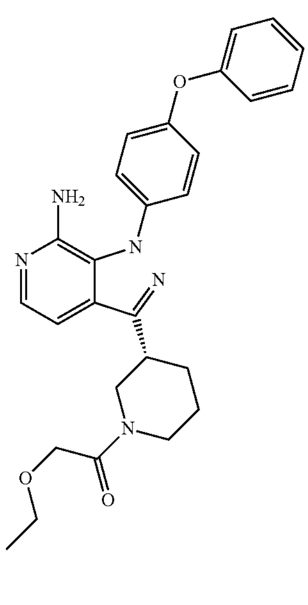 [SMILES: CCOCC(=O)N1CCC[C@@H](C(=N)c2ccnc(N)c2Nc2ccc(Oc3ccccc3)cc2)C1] | 3-[(3R)-1-(ethoxyacetyl)piperidin-3-yl]-1-(4-phenoxyphenyl)-1H-pyrazolo[3,4-c]pyridin-7-amine | Calc'd 472.2, found 472.2 | 1.01 |

TABLE 1-continued

| Example | Structure | IUPAC Name | Exact Mass [M + H]+ | Retention time (min) |
| --- | --- | --- | --- | --- |
| Example 17 | 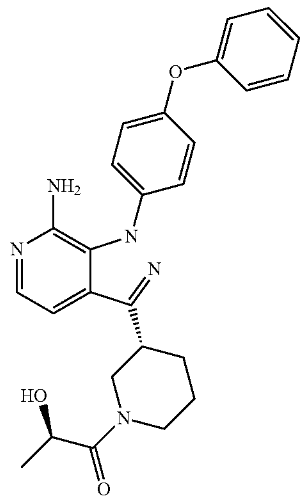 [SMILES: C[C@@H](O)C(=O)N1CCC[C@@H](C(=N)c2ccnc(N)c2Nc2ccc(Oc3ccccc3)cc2)C1] | (2R)-1-{(3R)-3-[7-amino-1-(4-phenoxyphenyl)-1H-pyrazolo[3,4-c]pyridin-3-yl]piperidin-1-yl}-1-oxopropan-2-ol | Calc'd 458.2, found 458.2 | 0.94 |
| Example 18 | 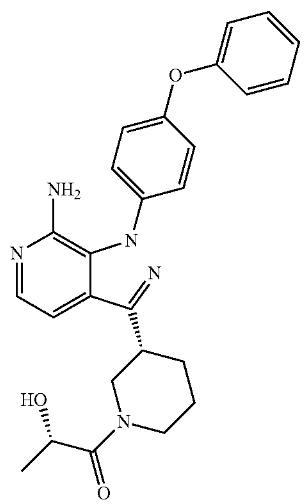 [SMILES: C[C@H](O)C(=O)N1CCC[C@@H](C(=N)c2ccnc(N)c2Nc2ccc(Oc3ccccc3)cc2)C1] | (2S)-1-{(3R)-3-[7-amino-1-(4-phenoxyphenyl)-1H-pyrazolo[3,4-c]pyridin-3-yl]piperidin-1-yl}-1-oxopropan-2-ol | Calc'd 458.2, found 458.2 | 0.94 |
| Example 19 | 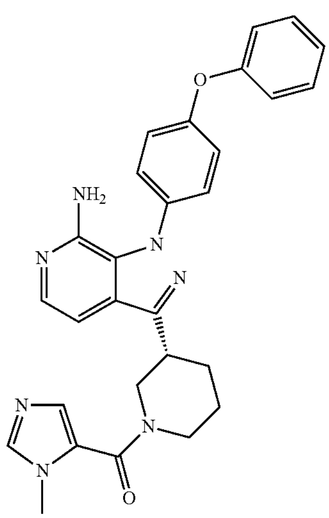 [SMILES: Cn1cncc1C(=O)N1CCC[C@@H](C(=N)c2ccnc(N)c2Nc2ccc(Oc3ccccc3)cc2)C1] | 3-{(3R)-1-[(1-methyl-1H-imidazol-5-yl)carbonyl]piperidin-3-yl}-1-(4-phenoxyphenyl)-1H-pyrazolo[3,4-c]pyridin-7-amine | Calc'd 494.2, found 494.2 | 0.78 |

TABLE 1-continued

| Example | Structure | IUPAC Name | Exact Mass [M + H]+ | Retention time (min) |
|---|---|---|---|---|
| Example 20 | 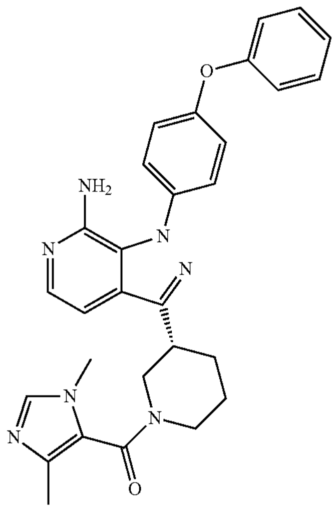 [SMILES: Cc1ncn(C)c1C(=O)N1CCC[C@@H](C(=N)c2ccnc(N)c2Nc2ccc(Oc3ccccc3)cc2)C1] | 3-{(3R)-1-[(1,4-dimethyl-1H-imidazol-5-yl)carbonyl]piperidin-3-yl}-1-(4-phenoxyphenyl)-1H-pyrazolo[3,4-c]pyridin-7-amine | Calc'd 508.2, found 508.2 | 0.79 |
| Example 21 | 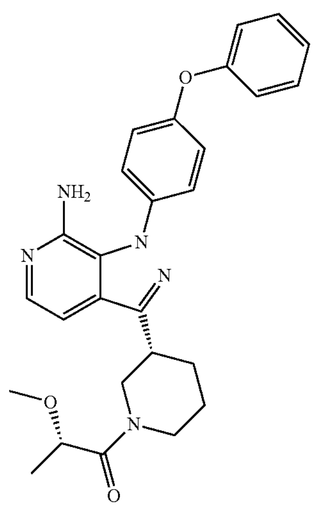 [SMILES: CO[C@@H](C)C(=O)N1CCC[C@@H](C(=N)c2ccnc(N)c2Nc2ccc(Oc3ccccc3)cc2)C1] | 3-{(3R)-1-[(2S)-2-methoxypropanoyl]piperidin-3-yl}-1-(4-phenoxyphenyl)-1H-pyrazolo[3,4-c]pyridin-7-amine | Calc'd 472.2, found 472.2 | 1.00 |
| Example 22 | 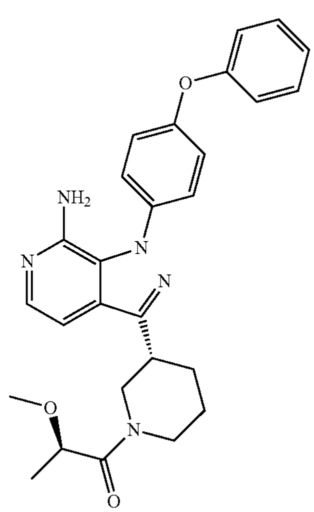 [SMILES: CO[C@H](C)C(=O)N1CCC[C@@H](C(=N)c2ccnc(N)c2Nc2ccc(Oc3ccccc3)cc2)C1] | 3-{(3R)-1-[(2R)-2-methoxypropanoyl]piperidin-3-yl}-1-(4-phenoxyphenyl)-1H-pyrazolo[3,4-c]pyridin-7-amine | Calc'd 472.2, found 472.2 | 1.00 |

TABLE 1-continued

| Example | Structure | IUPAC Name | Exact Mass [M + H]+ | Retention time (min) |
|---|---|---|---|---|
| Example 23 | 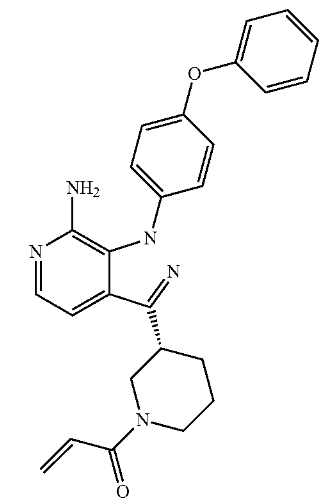 [SMILES: C=CC(=O)N1CCC[C@@H](C(=N)c2ccnc(N)c2Nc2ccc(Oc3ccccc3)cc2)C1] | 3-[(3R)-1-acryloylpiperidin-3-yl]-1-(4-phenoxyphenyl)-1H-pyrazolo[3,4-c]pyridin-7-amine | Calc'd 440.2, found 440.2 | 1.00 |
| Example 24 | 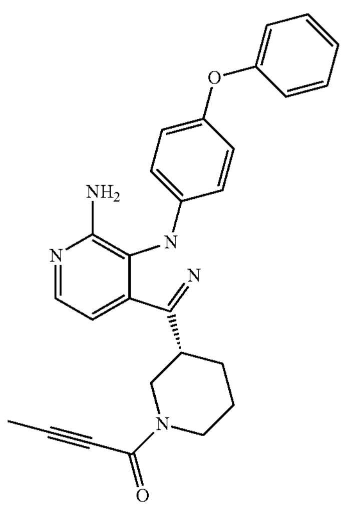 [SMILES: CC#CC(=O)N1CCC[C@@H](C(=N)c2ccnc(N)c2Nc2ccc(Oc3ccccc3)cc2)C1] | 3-[(3R)-1-but-2-ynoylpiperidin-3-yl]-1-(4-phenoxyphenyl)-1H-pyrazolo[3,4-c]pyridin-7-amine | Calc'd 452.2, found 452.2 | 1.05 |
| Example 25 | 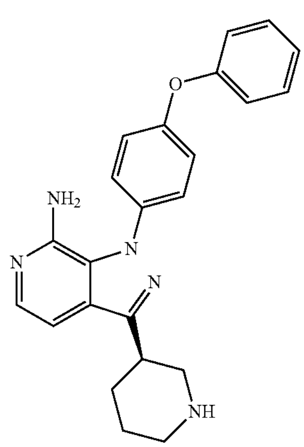 [SMILES: N=C(c1ccnc(N)c1Nc1ccc(Oc2ccccc2)cc1)[C@@H]1CCCNC1] | 1-(4-phenoxyphenyl)-3-[(3R)-piperidin-3-yl]-1H-pyrazolo[3,4-c]pyridin-7-amine | Calc'd 386.2, found 386.3 | 1.15 |

Example 26

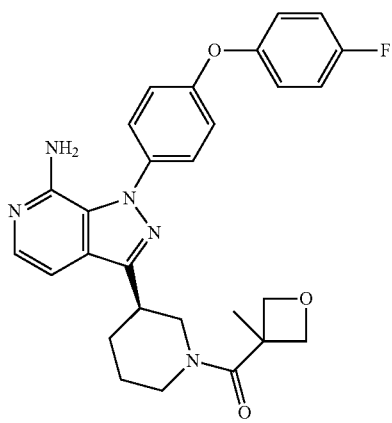 [SMILES: CC1(C(=O)N2CCC[C@@H](c3nn(-c4ccc(Oc5ccc(F)cc5)cc4)c4c(N)nccc34)C2)COC1]

(R)-(3-(7-amino-1-(4-(4-fluorophenoxy)phenyl)-1H-pyrazolo[3,4-c]pyridin-3-yl)piperidin-1-yl)(3-methyloxetan-3-yl)methanone In the same procedure as Example 1, using (4-(4-fluorophenoxy)phenyl)boronic acid in step 1 for the N-arylation, in five steps the title compound (R)-(3-(7-amino-1-(4-(4-fluorophenoxy)phenyl)-1H-pyrazolo[3,4-c]pyridin-3-yl)piperidin-1-yl)(3-methyloxetan-3-yl)methanone is prepared. LC-MS: $C_{28}H_{28}FN_5O_3$. found $[M+H]^+$ 502.3, RT=1.30 min.

Example 27

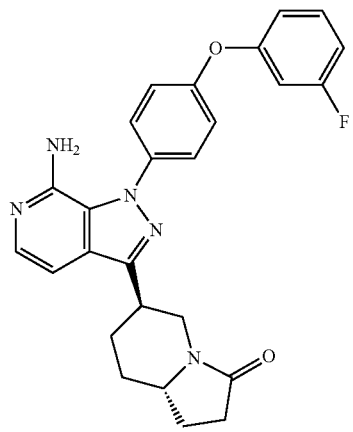 [SMILES: Nc1nccc2c([C@@H]3CC[C@H]4CCC(=O)N4C3)nn(-c3ccc(Oc4cccc(F)c4)cc3)c12]

(6R,8aS)-6-(7-amino-1-(4-(3-fluorophenoxy)phenyl)-1H-pyrazolo[3,4-c]pyridin-3-yl)hexahydroindolizin-3(2H)-one In the same procedure as Example 1, using (4-(3-fluorophenoxy)phenyl)boronic acid and (6R,8aS)-6-(7-chloro-1H-pyrazolo[3,4-c]pyridin-3-yl)hexahydroindolizin-3(2H)-one in step 1 for the N-arylation, in five steps the title compound (6R,8aS)-6-(7-amino-1-(4-(3-fluorophenoxy)phenyl)-1H-pyrazolo[3,4-c]pyridin-3-yl)hexahydroindolizin-3 (2H)-one is prepared. LC-MS: $C_{26}H_{24}FN_5O_2$. found $[M+H]^+$ 458.3, RT=1.30 min.

Example 28

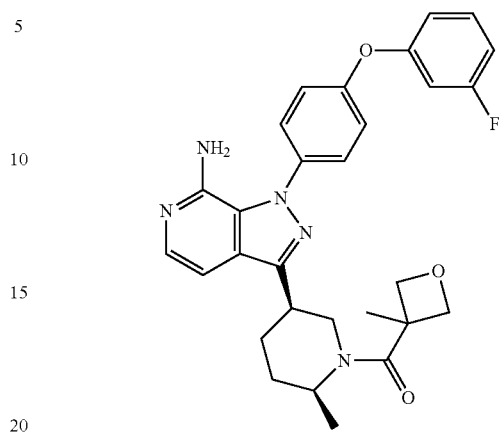

1-[4-(3-fluorophenoxy)phenyl]-3-{(3R,6S)-6-methyl-1-[(3-methyloxetan-3-yl)carbonyl]piperidin-3-yl}-1H-pyrazolo[3,4-c]pyridin-7-amine In the same procedure as Example 1, using (4-(3-fluorophenoxy)phenyl)boronic acid and (2 S,5R)-benzyl 5-(7-chloro-1H-pyrazolo[3,4-c]pyridin-3-yl)-2-methylpiperidine-1-carboxylate in step 1 for the N-arylation, in five steps the title compound 1-[4-(3-fluorophenoxy)phenyl]-3-{(3R,6S)-6-methyl-1-[(3-methyloxetan-3-yl)carbonyl]piperidin-3-yl}-1H-pyrazolo[3,4-c]pyridin-7-amine is prepared. LC-MS: $C_{29}H_{30}FN_5O_3$. found $[M+H]^+$ 516.4, RT=1.35 min.

Example 29

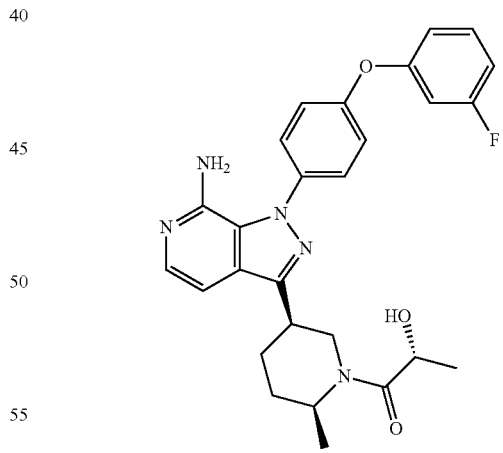

(2R)-1-[(2S,5R)-5-{7-amino-1-[4-(3-fluorophenoxy)phenyl]-1H-pyrazolo[3,4-c]pyridin-3-yl}-2-methylpiperidin-1-yl]-1-oxopropan-2-ol In the same procedure as Example 28, using (S)-2-hydroxypropanoic acid for the amide formation in step 4, in five steps the title compound (2R)-1-[(2S,5R)-5-{7-amino-1-[4-(3-fluorophenoxy)phenyl]-1H-pyrazolo[3,4-c]pyridin- 3-yl}-2-methylpiperidin-1-yl]-1-oxopropan-2-ol is prepared. LC-MS: $C_{27}H_{28}FN_5O_3$. found $[M+H]^+$ 490.4, RT=1.34 min.

Btk Enzyme Activity Assay Method

BTK enzymatic activity was determined with the LANCE (Lanthanide Chelate Excite) TR-FRET (Time-resolved fluorescence resonance energy transfer) assay. In this assay, the potency ($IC_{50}$) of each compound was determined from an eleven point (1:3 serial dilution; final compound concentration range in assay from 1 µM to 0.017 nM) titration curve using the following outlined procedure. To each well of a black non-binding surface Corning 384-well microplate (Corning Catalog #3820), 5 nL of compound (2000 fold dilution in final assay volume of 10 µL) was dispensed, followed by the addition of 7.5 µL of 1× kinase buffer (50 mM Hepes 7.5, 10 mM $MgCl_2$, 0.01% Brij-35, 1 mM EGTA, 0.05% BSA & 1 mM DTT) containing 5.09 pg/µL (66.67 pM) of BTK enzyme (recombinant protein from baculovirus-transfected Sf9 cells: full-length BTK, 6HIS-tag cleaved). Following a 60 minute compound & enzyme incubation, each reaction was initiated by the addition of 2.5 µL 1× kinase buffer containing 8 µM biotinylated "A5" peptide (Biotin-EQEDEPEGDYFEWLE-NH2), and 100 µM ATP. The final reaction in each well of 10 µL consists of 50 pM hBTK, 2 µM biotin-A5-peptide, and 25 µM ATP. Phosphorylation reactions were allowed to proceed for 120 minutes. Reactions were immediately quenched by the addition of 20 uL of 1× quench buffer (15 mM EDTA, 25 mM Hepes 7.3, and 0.1% Triton X-100) containing detection reagents (0.626 nM of LANCE-Eu-W1024-anti-phosphoTyrosine antibody, PerkinElmer and 86.8 nM of Streptavidin-conjugated Dylight 650, Dyomics/ThermoFisher Scientific). After 60 minutes incubation with detection reagents, reaction plates were read on a PerkinElmer EnVision plate reader using standard TR-FRET protocol. Briefly, excitation of donor molecules (Eu-chelate:anti-phospho-antibody) with a laser light source at 337 nm produces energy that can be transferred to Dylight-650 acceptor molecules if this donor:acceptor pair is within close proximity. Fluorescence intensity at both 665 nm (acceptor) and 615 nm (donor) are measured and a TR-FRET ratio calculated for each well (acceptor intensity/donor intensity). $IC_{50}$ values were determined by 4 parameter robust fit of TR-FRET ratio values vs. ($Log_{10}$) compound concentrations.

The following Table provides specific 1050 values for the examples. The 1050 values set forth below were determined according to the Assay Method described above.

TABLE 2

Compounds BTK binding potency

| Example number | BTK binding IC50 (nM) |
| --- | --- |
| Example 1 | 1.7 |
| Example 2 | 2.0 |
| Example 3 | 3.3 |
| Example 4 | 9.3 |
| Example 5 | 3.0 |
| Example 6 | 13.7 |
| Example 7 | 1.8 |
| Example 8 | 3.3 |
| Example 9 | 8.9 |
| Example 10 | 11.8 |
| Example 11 | 2.7 |
| Example 12 | 3.7 |
| Example 13 | 3.5 |
| Example 14 | 2.0 |
| Example 15 | 3.5 |
| Example 16 | 3.5 |
| Example 17 | 1.0 |
| Example 17 | 1.0 |
| Example 18 | 2.3 |
| Example 19 | 2.7 |
| Example 20 | 9.2 |
| Example 21 | 3.9 |
| Example 22 | 5.5 |
| Example 23 | 0.66 |
| Example 24 | 1.0 |
| Example 25 | 30.8 |
| Example 26 | 56.9 |
| Example 27 | |
| Example 28 | 3.8 |
| Example 29 | 5.8 |

What is claimed is:
1. A compound according to Formula I, or a pharmaceutically acceptable salt thereof

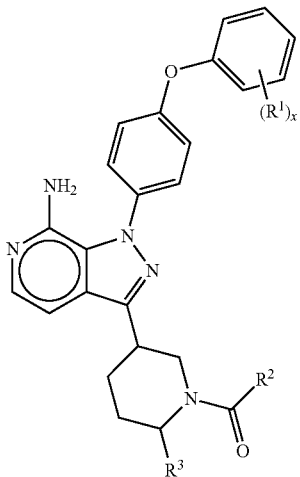

Formula I wherein:
R¹ is halogen;
R² is selected from the group consisting of
 a) OH;
 b) (1-6C)alkyl;
 c) (3-6C)cycloalkyl;
 d) (1-6C)alkoxy;
 e) (1-3C)heterocycloalkyl; and
 f) (1-3C)heteroaryl;
 g) (2-4C)alkenyl; and
 h) (2-4C)alkynyl;
R² is optionally substituted with one, two or three groups selected from: halogen, (1-6C)alkyl, (1-6C)alkoxy, hydroxy or cyano;
R³ is H or (1-3C)alkyl;
R² and R³ together can form a saturated heterocyclic 5- or 6-membered ring; and
x is 0 or 1.

2. The compound of claim 1, wherein R¹ is fluorine.
3. The compound of claim 1, wherein R³ is CH₃.
4. A compound selected from:
3-{(3R)-1-[(3-methyloxetan-3-yl)carbonyl]piperidin-3-yl}-1-(4-phenoxyphenyl)-1H-pyrazolo[3,4-c]pyridin-7-amine;
1-(4-phenoxyphenyl)-3-[(3R)-1-propanoylpiperidin-3-yl]-1H-pyrazolo[3,4-c]pyridin-7-amine;
3-[(3R)-1-(cyclopropylcarbonyl)piperidin-3-yl]-1-(4-phenoxyphenyl)-1H-pyrazolo[3,4-c]pyridin-7-amine;
3-{(3R)-1-[(2,2-difluorocyclopropyl)carbonyl]piperidin-3-yl}-1-(4-phenoxyphenyl)-1H-pyrazolo[3,4-c]pyridin-7-amine;
1-({(3R)-3-[7-amino-1-(4-phenoxyphenyl)-1H-pyrazolo[3,4-c]pyridin-3-yl]piperidin-1-yl} carbonyl)cyclopropanol;
3-{(3R)-1-[(3,5-dimethylisoxazol-4-yl)carbonyl]piperidin-3-yl}-1-(4-phenoxyphenyl)-1H-pyrazolo[3,4-c]pyridin-7-amine;
3-[(3R)-1-(3-methoxypropanoyl)piperidin-3-yl]-1-(4-phenoxyphenyl)-1H-pyrazolo[3,4-c]pyridin-7-amine;
3-{(3R)-1-[(1-methylcyclopropyl)carbonyl]piperidin-3-yl}-1-(4-phenoxyphenyl)-1H-pyrazolo[3,4-c]pyridin-7-amine;
3-{(3R)-1-[(3,3-difluorocyclobutyl)carbonyl]piperidin-3-yl}-1-(4-phenoxyphenyl)-1H-pyrazolo[3,4-c]pyridin-7-amine;
1-({(3R)-3-[7-amino-1-(4-phenoxyphenyl)-1H-pyrazolo[3,4-c]pyridin-3-yl]piperidin-1-yl}carbonyl)cyclopropanecarbonitrile;
3-[(3R)-1-(methoxyacetyl)piperidin-3-yl]-1-(4-phenoxyphenyl)-1H-pyrazolo[3,4-c]pyridin-7-amine;
3-[(3R)-1-(2-methylpropanoyl)piperidin-3-yl]-1-(4-phenoxyphenyl)-1H-pyrazolo[3,4-c]pyridin-7-amine;
3-[(3R)-1-(cyclobutylcarbonyl)piperidin-3-yl]-1-(4-phenoxyphenyl)-1H-pyrazolo[3,4-c]pyridin-7-amine;
3-[(3R)-1-acetylpiperidin-3-yl]-1-(4-phenoxyphenyl)-1H-pyrazolo[3,4-c]pyridin-7-amine;
3-{(3R)-1-[(2-methoxyethoxy)acetyl]piperidin-3-yl}-1-(4-phenoxyphenyl)-1H-pyrazolo[3,4-c]pyridin-7-amine;
3-[(3R)-1-(ethoxyacetyl)piperidin-3-yl]-1-(4-phenoxyphenyl)-1H-pyrazolo[3,4-c]pyridin-7-amine;
(2R)-1-{(3R)-3-[7-amino-1-(4-phenoxyphenyl)-1H-pyrazolo[3,4-c]pyridin-3-yl]piperidin-1-yl}-1-oxopropan-2-ol;
(2S)-1-{(3R)-3-[7-amino-1-(4-phenoxyphenyl)-1H-pyrazolo[3,4-c]pyridin-3-yl]piperidin-1-yl}-1-oxopropan-2-ol;
3-{(3R)-1-[(1-methyl-1H-imidazol-5-yl)carbonyl]piperidin-3-yl}-1-(4-phenoxyphenyl)-1H-pyrazolo[3,4-c]pyridin-7-amine;
3-{(3R)-1-[(1,4-dimethyl-1H-imidazol-5-yl)carbonyl]piperidin-3-yl}-1-(4-phenoxyphenyl)-1H-pyrazolo[3,4-c]pyridin-7-amine;
3-{(3R)-1-[(2S)-2-methoxypropanoyl]piperidin-3-yl}-1-(4-phenoxyphenyl)-1H-pyrazolo[3,4-c]pyridin-7-amine;
3-{(3R)-1-[(2R)-2-methoxypropanoyl]piperidin-3-yl}-1-(4-phenoxyphenyl)-1H-pyrazolo[3,4-c]pyridin-7-amine;
3-[(3R)-1-acryloylpiperidin-3-yl]-1-(4-phenoxyphenyl)-1H-pyrazolo[3,4-c]pyridin-7-amine;
3-[(3R)-1-but-2-ynoylpiperidin-3-yl]-1-(4-phenoxyphenyl)-1H-pyrazolo[3,4-c]pyridin-7-amine;
1-[4-(4-fluorophenoxy)phenyl]-3-{(3R)-1-[(3-methyloxetan-3-yl)carbonyl]piperidin-3-yl}-1H-pyrazolo[3,4-c]pyridin-7-amine;
(6R,8aS)-6-{7-amino-1-[4-(3-fluorophenoxy)phenyl]-1H-pyrazolo[3,4-c]pyridin-3-yl}hexahydroindolizin-3(2H)-one;
1-[4-(3-fluorophenoxy)phenyl]-3-{(3R,6 S)-6-methyl-1-[(3-methyloxetan-3-yl)carbonyl]piperidin-3-yl}-1H-pyrazolo[3,4-c]pyridin-7-amine; and
(2R)-1-[(2S,5R)-5-{7-amino-1-[4-(3-fluorophenoxy)phenyl]-1H-pyrazolo[3,4-c]pyridin-3-yl}-2-methylpiperidin-1-yl]-1-oxopropan-2-ol;
or a pharmaceutically acceptable salt thereof.

5. The compound of claim 1 or a pharmaceutically acceptable salt thereof for use in the treatment of Bruton's Tyrosine Kinase (Btk) mediated disorders.
6. A pharmaceutical composition which comprises the compound of claim 1 or a pharmaceutically acceptable salt thereof and one or more pharmaceutically acceptable excipients.
7. The pharmaceutical composition of claim 6, which further comprises at least one additional therapeutically active agent.
8. A method for treating a subject suffering with a Bruton's Tyrosine Kinase (Btk) mediated disorder comprising administering to the subject the compound of claim 1 in an amount effective to treat the Btk mediated disorder, thereby treating the subject.

9. The method of claim 8, wherein the Btk mediated disorder is selected from the group consisting of rheumatoid arthritis, psoriatic arthritis, infectious arthritis, progressive chronic arthritis, deforming arthritis, osteoarthritis, traumatic arthritis, gouty arthritis, Reiter's syndrome, polychondritis, acute synovitis and spondylitis, glomerulonephritis (with or without nephrotic syndrome), autoimmune hematologic disorders, hemolytic anemia, aplasic anemia, idiopathic thrombocytopenia, and neutropenia, autoimmune gastritis, and autoimmune inflammatory bowel diseases, ulcerative colitis, Crohn's disease, host versus graft disease, allograft rejection, chronic thyroiditis, Graves' disease, schleroderma, diabetes (type I and type II), active hepatitis (acute and chronic), pancreatitis, primary billiary cirrhosis, myasthenia gravis, multiple sclerosis, systemic lupus erythematosis, psoriasis, atopic dermatitis, contact dermatitis, eczema, skin sunburns, vasculitis, chronic renal insufficiency, Stevens-Johnson syndrome, inflammatory pain, idiopathic sprue, cachexia, sarcoidosis, Guillain-Barré syndrome, uveitis, conjunctivitis, kerato conjunctivitis, otitis media, periodontal disease, pulmonary interstitial fibrosis, asthma, bronchitis, rhinitis, sinusitis, pneumoconiosis, pulmonary insufficiency syndrome, pulmonary emphysema, pulmonary fibrosis, silicosis, chronic inflammatory pulmonary disease, and chronic obstructive pulmonary disease.

10. The method of claim 9, wherein the Btk mediated disorder is rheumatoid arthritis, psoriatic arthritis, or osteoarthritis.

\* \* \* \* \*